(12) United States Patent
Lopaschuk et al.

(10) Patent No.: US 7,074,828 B2
(45) Date of Patent: Jul. 11, 2006

(54) COMPOUNDS THAT STIMULATE GLUCOSE UTILIZATION AND METHODS OF USE

(75) Inventors: Gary David Lopaschuk, Edmonton (CA); John Christopher Vederas, Edmonton (CA); Jason Roland Dyck, Sherwood Park (CA)

(73) Assignee: The Governors of the University of Alberta, Edmonton (CA)

( * ) Notice: Subject to any disclaimer, the term of this patent is extended or adjusted under 35 U.S.C. 154(b) by 0 days.

(21) Appl. No.: 10/313,990

(22) Filed: Dec. 5, 2002

(65) Prior Publication Data

US 2004/0116517 A1    Jun. 17, 2004

Related U.S. Application Data

(63) Continuation-in-part of application No. 10/181,274, filed on Apr. 9, 2003.

(51) Int. Cl.
   *A61K 31/21* (2006.01)
   *C07C 69/76* (2006.01)

(52) U.S. Cl. ............ 514/531; 514/529; 560/123; 560/124

(58) Field of Classification Search ........... 560/124, 560/123; 514/531, 529
See application file for complete search history.

(56) References Cited

U.S. PATENT DOCUMENTS

| | | | |
|---|---|---|---|
| 3,306,727 A | 2/1967 | Neighbors | |
| 3,926,860 A * | 12/1975 | Chappell | 512/8 |
| 3,957,849 A | 5/1976 | Henrick et al. | 260/468 H |
| 4,000,315 A | 12/1976 | Henrick et al. | 424/305 |

FOREIGN PATENT DOCUMENTS

WO    WO 02/085294    10/2002

OTHER PUBLICATIONS

Bersin, et al., Dichloroacetate as metabolic therapy for myocardial ischemia and failure, American Heart Journal, 134(5)(Part 1):841-855 (1997).
Burger, et al., Database Crossfire Beilstein 'Online! Beilstein Institute zur Forderung der Chemischen Wissenschaften, Frankfurt am Main, DE; Database accession No. 2576757, XP002248454 (Abstract) J. Med. Chem.., vol. 6, 1963, pp. 221-227.
Calderon, et al., Database Crossfire Beilstein 'Online! Beilstein Institute zur Forderung der Chemischen Wissenschaften, Frankfurt am Main, DE; Database accession No. 7079339 XP002248456 (Abstract) J. Med. Chem., vol. 37, No. 15, 1994, pp. 2285-2291.
Database CA 'Online! Chemical Abstracts Service, Columbus, Ohio, US; Henrick, et al., "Ovicidal activity and its relation to chemical structure for the two-spotted spider mite (Tetranychus urticae Koch) in a new class of miticides contaiing the cyclopropyl group", retrieved from STN Database accession No. 85:105335 CA XP002249230 s. RN 60128-48-5, RN 60128-46-3 abstract & Journal of Agricultural and Food Chemistry (1976), 24(5), 1023-9.
Whitten, et al, Database Crossfile Beilstein 'Online! Beilstein Institute zur Forderung der Chemischen Wissenschaften, Frankfurt am Main, DE; Database accession No. 2040782 XP002248455 Abstract J. Med. Chem., vol 39, No. 22, 1996, pp. 4354-4357.
Barak, C., et al., Effects of dichloroacetate on mechanical recovery and oxidation of physiologic substrates after ischemia and reperfusion in the isloated heart, J Cardiovasc Pharmacol 31: 336-44., 1998.
Barbour, R.L., et al.,.Use of gated perfusion to study early effects of anoxia on cardiac energy metabolism: A new $^{31}P$ NMR method *Biochemistry* 1923:6503-6062, 1984.
Chen, T.M., et al., Effects of insulin on glucose uptake by rat hearts during and after coronary flow reduction, Am J Physiol 273: H2170-7., 1997.
Fraser, H., et al., Assessment of glycogen turnover in aerobic, ischemic, and reperfused working rat hearts, Am J Physiol 275: H1533-41, 1998.
Fraser, H., et al., Alteration of glycogen and glucose metabolism in ischaemic and post-ischaemic working rat hearts by adenosine $A_1$ receptor stimulation, Br J Pharmacol 128: 197-205, 1999.
Gamble, J., et al., Glycolysis and glucose oxidation during reperfusion of Ischemic hearts from diabetic rats, Biochimica et Biophysica Acta 1225: 191-9, 1994.
Itoi, T. et al., The contribution of glycolysis, glucose oxidation, lactate oxidation, and fatty acid oxidation to ATP production in isolated biventricular working hearts from 2-week-old rabbits, Pediatric Research 34: 735-41, 1993.

(Continued)

*Primary Examiner*—Zinna Northington Davis
(74) *Attorney, Agent, or Firm*—Pillsbury Winthrop Shaw Pittman LLP

(57) ABSTRACT

The invention provides novel compounds of the Formula (I) that stimulate rates of glucose oxidation in myocardial cells:

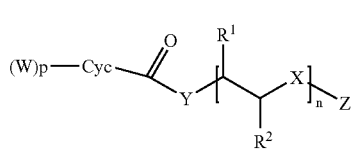

Formula I wherein W, Cyc, p, Y, X, Z, R, $R^1$, $R^2$, $R^3$, $R^4$, i and n are as defined for Formula (I) herein. The invention also relates to pharmaceutical compositions comprising compounds capable of stimulation of glucose oxidation, methods for increasing glucose oxidation rates in myocardial cells, and methods of treatment of myocardial ischemia.

31 Claims, 4 Drawing Sheets

OTHER PUBLICATIONS

Jonassen, A.K., et al., *Glucose-insulin-potassium reduces infarct size when administered during reperfusion*, Cardiovasc Drugs Ther 14: 615-23., 2000.

Kantor, P.F., et al., The antianginal drug trimetazidine shifts cardiac energy metabolism from fatty acid oxidation to glucose oxidation by inhibiting mitochondrial long-chain 3-ketoacryl coenzyme A thiolase, Circulation Research. 86: 580-8, 2000.

King, L.M., et al., Glucose delivery is a major determinant of glucose utilisation in the ischemic myocardium with a residual coronary flow, Cardiovasc Res 39: 381-92., 1998.

Kudo, N., et al., Characterization of 5'AMP-activated protein kinase activity in the heart and its role in inhibiting acetyl-CoA carboxylas during reperfusion following ischemia, Biochimica et Biophysica Acta 1301: 67-75, 1996.

Kudo, N., et al., High rates of fatty acid oxidation during reperfusion of ischemic hearts are associated with a decrease in malonyl-CoA levels due to an increase in 5'-AMP-activated protein kinase inhibition of acetyl-CoA carboxylase, Journal of Biological Chemistry 270(29): 17513-20, 1995.

Lopaschuk, G.D., et al., Plasma fatty acid levels in infants and adults after myocardial ischemia, Am Heart J 128: 61-7, 1994.

Lopaschuk, G.D., et al., R gulation of carbohydrat metabolism in ischemia and reperfusion, Am Heart J 139: S115-9., 2000.

Lopaschuk, G.D., et al., Alterations in fatty acid oxidation during reperfusion of th heart after myocardial ischemia, Am J Cardiol 80: 11A-16A, 1997.

Lopaschuk, G.D., et al., Treating ischemic heart disease by pharmacologically improving cardiac energy metabolism, Am J Cardiol 82: 14K-17K., 1998.

Lopaschuk, G.D., et al., Response of isolated working hearts to fatty acids and carnitine palmitoyltransferase 1 inhibition during reduction of coronary flow in acutely and chronically diabetic rats, Circ Res 65: 378-87, 1989.

Lopaschuk, G.D., et al., Glucose and palmitate oxidation in isolated working rat hearts reperfused after a period of transient global ischemia, Circ Res 66: 546-53, 1990.

Lopaschuk, G.D., et al., Glucose metabolism in the ischemic heart, Circulation 95: 313-5., 1997.

Lopaschuk, G.D., et al., Optimizing cardiac energy metabolism: How can fatty acid and carbohydrate metabolism be manipuated?, Coron Artery Dis 12: S8-11., 2001.

Lopaschuk, G.D., et al., Measurements of fatty acid and carbohydrate metabolism in the isolated working rat heart, Molecular & Cellular Biochemistry 172: 137-47, 1997.

Lopaschuk, G.D., et al., Glucose oxidation is stimulated in reperfused ischemic hearts with the carnitine palmitoyltransferase 1 inhibitor, Etomoxir, Molecular & Cellular Biochemistry 88: 175-9, 1989.

McCormack, J.G., et al., Ranolazine stimulates glucose oxidation in normoxic, ischemic, and reperfused ischemic rat hearts, Circulation 93: 135-42., 1996.

McCormack, J.G., et al., Ranolazine: A novel metobolic modulator for the treatment of angina, Gen Pharmacol 30(5): 639-45., 1998.

McVeigh, J.J., et al, Dichloroacetate stimulation of glucose oxidation improves recovery of ischemic rat hearts, American Journal of Physiology 259: H1079-85, 1990.

Nicholl, T.A., et al., Effects of free fatty acids and dichloroacetate on isolated working diabetic rat heart, American Journal of Physiology 261: H1053-9, 1991.

Pogatsa, G., Metabolic energy metabolism in diabetes: therapeutic implications, Coron Artery Dis 12: S29-33., 2001.

Saddik, M., et al., Myocardial triglyceride turnover during reperfusion of isolated rat hearts subjected to a transient period of global ischemia, J Bio Chem. 1992; 267(6):3825-3831.

Stanley, W.C., et al., Cardiac energetics during ischaemia and the rationale for metabolic interventions, Coron Artery Dis 12: S3-7., 2001.

Taniguchi, M., et al., Dichloroacetate improves cardiac efficiency after ischemia independent of changes in mitochondrial proton leak, Am J Physiol Heart Circ Physiol 280: H1762-9., 2001.

Vaghaiwalla, F., et al., Trimetazidine-induced enhancement of myocardial glucose utilization in normal and ischemic myocardial tissue: An evaluation by positron emission tomography, Am J Cardiol 82: 42K-49K., 1998.

Wambolt, R.B., et al., Dichloroacetate improves postischemic function of hypertrophied rat hearts, J Am Coll Cardiol 36: 1378-85., 2000.

Yamane, Y., et al., *Stimulated glucose uptake in the ischemic border zone: Its dependence on glucose uptake in the normally perfused area*, J Nucl Med 38: 1515-21., 1997.

* cited by examiner

COMPOUNDS THAT STIMULATE GLUCOSE UTILIZATION AND METHODS OF USE

This patent application is a continuation-in-part of U.S. Ser. No. 10/181,274 filed Apr. 9, 2003 which is a U.S. National filing under 35 U.S.C. 371 which is based on PCT/IB02/02525, filed Apr. 1, 2002, now withdrawn, the entirety of the disclosure of each of these applications which is hereby incorporated into the present application by reference.

FIELD OF THE INVENTION

The invention relates to novel compounds that stimulate rates of glucose oxidation in myocardial cells. The invention also relates to pharmaceutical compositions comprising compounds capable of stimulating glucose oxidation, methods for increasing glucose oxidation rates in myocardial cells, and methods of treatment of myocardial ischemia.

BACKGROUND OF THE INVENTION

Myocardial ischemia is a common clinical pathology that occurs in the setting of angina pectoris, acute myocardial infarction, or during cardiac surgery. Myocardial ischemia is a major clinical problem, with its complications being the major cause of mortality and morbidity in Western society.

It has been reported that stimulating glucose oxidation both during and following ischemia can benefit the ischemic heart. *Br J Pharmacol* 128: 197–205, 1999, *Am J Physiol* 275: H1533–41, 1998. *Biochimica et Biophysica Acta* 1225: 191–9, 1994, *Pediatric Research* 34: 735–41, 1993, *Journal of Biological Chemistry* 270: 17513–20, 1995. *Biochimica et Biophysica Acta* 1301: 67–75, 1996, *Am J Cardiol* 80: 11A–16A, 1997, *Molecular & Cellular Biochemistry* 88: 175–9, 1989, *Circ Res* 65: 378–87, 1989, Circ Res 66: 546–53, 1990, *American Journal of Physiology* 259: H1079–85, 1990, *American Journal of Physiology* 261: H1053–9, 1991, *Am J Physiol Heart Circ Physiol* 280: H1762–9., 2001, *J Am Coll Cardiol* 36: 1378–85., 2000.

To meet the high energy demands of the contracting muscle, the heart must produce a constant and plentiful supply of the free energy carrier, adenosine triphosphate (ATP). This energy is produced by the metabolism of a variety of carbon substrates, including carbohydrates such as glucose. The metabolism of fatty acid is the other major source of energy for the heart.

Glucose metabolism in the heart consists of two important pathways, namely glycolysis and glucose oxidation.

It has been shown that during ischemia (such as that produced by angina pectoris, myocardial infarction or heart surgery) the levels of circulating fatty acids in the plasma can be dramatically elevated. *Am Heart J* 128: 61–7, 1994. As a result, during ischemia and reperfusion the heart is exposed to high levels of fatty acids, which results in the preferential use of fatty acids as an oxidative substrate over glucose. It further has been reported that this over-reliance on fatty acids as a major source of ATP contributes to fatty acid-induced ischemic damage. This observation has sparked numerous approaches directed at switching substrate utilization back to glucose in an attempt to protect the heart from fatty acid-induced ischemic damage. *J Cardiovasc Pharmacol* 31: 336–44., 1998, *Am Heart J* 134: 841–55., 1997, *Am J Physiol* 273: H2170–7., 1997, *Cardiovasc Drugs Ther* 14: 615–23., 2000, *Cardiovasc Res* 39: 381–92., 1998, *Am Heart J* 139: S115–9., 2000, *Coron Artery Dis* 12: S8–11., 2001, *Am J Cardiol* 82: 14K–17K., 1998, *Molecular & Cellular Biochemistry* 172: 137–47, 1997, *Circulation* 95: 313–5., 1997, *Gen Pharmacol* 30: 639–45., 1998, *Am J Cardiol* 82: 42K–49K., 1998, *Coron Artery Dis* 12: S29–33., 2001, *Coron Artery Dis* 12: S3–7., 2001, *J Nucl Med* 38: 1515–21., 1997. Current approaches that are used to manipulate myocardial energy metabolism involve either stimulating glucose metabolism directly or indirectly (i.e., inhibiting fatty acid metabolism).

Since high fatty acid oxidation rates markedly decrease glucose oxidation, one approach to increasing glucose oxidation is to inhibit fatty acid oxidation. This has proven effective both during and following ischemia, and this pharmacological approach is starting to see clinical use. Although a number of pharmacological agents designed to inhibit fatty acid oxidation have recently been developed, the direct β-oxidation inhibitor, trimetazidine, was the first anti-anginal agent widely used that has a mechanism of action that can be attributed to an optimization of energy metabolism *Circulation Research*. 86: 580–8, 2000.

Trimetazidine is reported to primarily act by inhibiting fatty acid oxidation, thereby stimulating glucose oxidation in the heart.

A second clinically effective agent that is reported to switch energy metabolism from fatty acid to glucose oxidation is ranolazine. It has been reported-that this agent stimulates glucose oxidation secondary to an inhibition of fatty acid oxidation *Circulation* 93: 135–42., 1996.

The detrimental effects of fatty acids on mechanical function during and following ischemia may also be attenuated by agents that increase glucose oxidation directly. Numerous experimental studies have reported that stimulation of glucose oxidation by using dichloroacetate (DCA) following ischemia (at the expense of fatty acids) can benefit the ischemic heart. *Am Heart J* 134: 841–55, 1997. Although DCA is an effective compound designed to stimulate glucose oxidation, it has a short biological half-life.

Therefore, there is need to develop novel class of compounds and to identify compounds that can stimulate glucose oxidation, have long biological life, and be effective in treatment or prevention of myocardial ischemia

SUMMARY OF THE INVENTION

In one aspect, the present invention is directed to novel compounds represented by Formula (I):

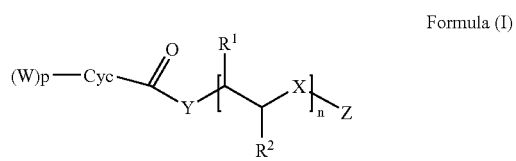

Formula (I)

wherein
W is $C_1$–$C_6$ alkyl, halogen, or aryl;
Cyc is $C_3$ or $C_4$ cycloalkyl;
p is an integer from 0 to 3 when Cyc is $C_4$ cycloalkyl, and p is an integer from 0 to 2 when Cyc is $C_3$ cycloalkyl;
Y is O, S, or NR;
X is O, S, NR, or $CR^3R^4$;
Z is H, alkyl, cycloalkyl, aryl or (cyclo)alkylcarbonyl or

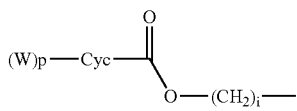

if X is NR and R is

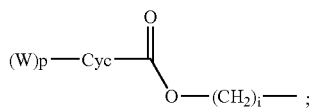

R is H, alkyl, aryl, or

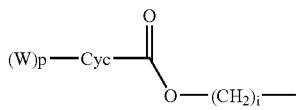

where i is an integer from 2 to 4;
$R^1$ is H, alkyl or aryl;
$R^2$ is H, alkyl, aryl or O;
$R^3$ and $R^4$ are independently H, alkyl or aryl; and n is an integer from 1 to 10; or a pharmaceutically acceptable salt, ester or prodrug thereof.

In one alternate preferred aspect, the present invention is directed to novel compounds of Formula (I) which are represented by Formula (Ia):

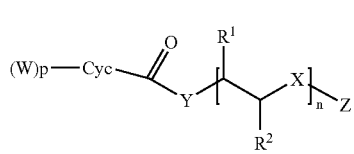

Formula (Ia)

wherein
W is $C_1$–$C_6$ alkyl, halogen, or aryl;
Cyc is $C_3$ or $C_4$ cycloalkyl;
p is an integer from 0 to 3 when Cyc is $C_4$ cycloalkyl, and p is an integer from 0 to 2 when Cyc is $C_3$ cycloalkyl;
Y is O, S, or NR;
X is O, S, NR, or $CR^3R^4$;
Z is H, alkyl, cycloalkyl, aryl or (cyclo)alkylcarbonyl;
R is H, alkyl or aryl;
$R^1$ is H, alkyl or aryl;
$R^2$ is H, alkyl, aryl or O;
$R^3$ and $R^4$ are independently H, alkyl or aryl; and
n is an integer from 1 to 10;
or a pharmaceutically acceptable salt, ester or prodrug thereof.

According to one aspect, the present invention is further directed to methods for increasing or improving glucose utilization in myocardial or other types of cells, tissue or organs of warm blooded animals, especially those which are capable of high glucose metabolism (e.g., heart and other muscles). The method comprises treating cells, tissue or organs with substituted or unsubstituted cyclopropane carboxylic acid or cyclobutane carboxylic acid represented by the Formula (II):

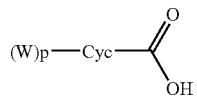

Formula (II)

wherein W, Cyc and p are as defined in connection with Formula (I), or a cyclopropane carboxylic acid or cyclobutane carboxylic derivative of Formula (I).

According to an alternate aspect, the present invention is also directed to pharmaceutical compositions comprising a compound according to the Formula (I) and suitable pharmaceutical carriers, excipients or fillers.

According to a further aspect, the present invention is directed to a method of treating physiological conditions or disorders that may be effectively treated by increasing of cell glucose utilization. According to one embodiment, such method comprises administering to a patient in need of such treatment an effective amount of a pharmaceutical composition comprising substituted or unsubstituted cyclopropane carboxylic acid or cyclobutane carboxylic acid according to Formula (II) or a cyclopropane carboxylic acid or cyclobutane carboxylic acid derivative of Formula (I).

The present invention is further directed to kits including a pharmaceutical composition according to the present invention.

The methods of the present invention are applicable for treating warm blooded animal subjects, such as mammals, including humans, primates, etc.

DEFINITIONS

As used herein, the term "alkyl" means straight or branched alkane chain, which may be, optionally substituted with, for example, halogens, cyclic or aromatic substituents.

As used herein, the terms "aryl" or "aromatic" refer to mono- and bi-cyclic structures comprising 5 to 12 carbon atoms, preferably monocyclic rings containing six carbon atoms. The ring may be optionally substituted with alkyl, alkenyl, halogen, alkoxy, or haloalkyl substituents.

DETAILED DESCRIPTION OF THE INVENTION

Figure 1:
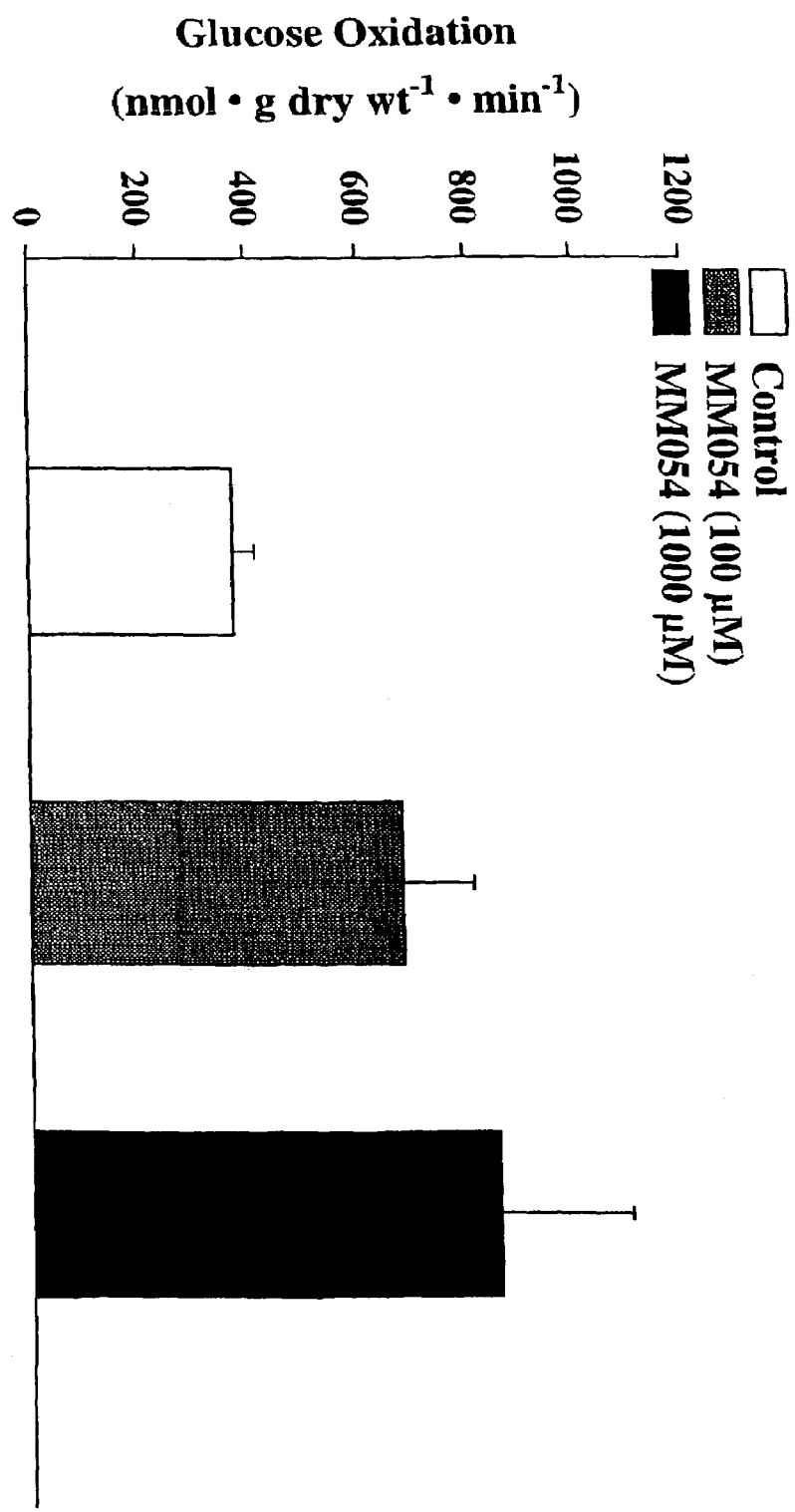
FIG. 1 is a graph which depicts glucose oxidation in an isolated perfused working rat heart model at the indicated concentrations of cyclopropanecarboxylic acid, 2-[2-(2-methoxy-ethoxy)-ethoxy]-ethyl ester (MM054) as compared to a control.

According to one aspect, the present invention provides novel compounds which are derivatives of a cyclopropane carboxylic acid or a cyclobutane carboxylic acid. These compounds exhibit glucose oxidation stimulating activity in myocardial cells and other types of cells. The compounds according to the present invention are represented by the Formula (I):

Formula (I)

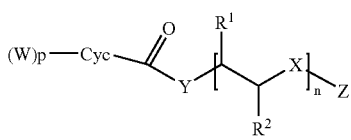

wherein

W is $C_1$–$C_6$ alkyl, halogen, or aryl;

Cyc is $C_3$ or $C_4$ cycloalkyl;

p is an integer from 0 to 3 when Cyc is $C_4$ cycloalkyl, and p is an integer from 0 to 2 when Cyc is $C_3$ cycloalkyl;

Y is O, S, or NR,

X is O, S, NR, or $CR^3R^4$;

Z is H, alkyl, cycloalkyl, aryl or (cyclo)alkyl carbonyl or if X is NR and R is

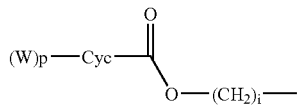

R is H, alkyl, aryl or where i is an integer from 2 to 4;

$R^1$ is H, alkyl or aryl;

$R^2$ is H, alkyl, aryl or O;

$R^3$ and $R^4$ are independently H, alkyl or aryl and n is an integer from 1 to 10;

or a pharmaceutically acceptable salt, ester or prodrug thereof.

According to an alternate aspect, the present invention provides novel compounds of Formula (I) according to the present invention which are represented by Formula (Ia):

Formula (Ia)

wherein

W is $C_1$–$C_6$ alkyl, halogen, or aryl;

Cyc is $C_3$ or $C_4$ cycloalkyl;

p is an integer from 0 to 3 when Cyc is $C_4$ cycloalkyl, and p is an integer from 0 to 2 when Cyc is $C_3$ cycloalkyl;

Y is O, S, or NR,

X is O, S, NR, or $CR^3R^4$;

Z is H, alkyl, cycloalkyl, aryl or (cyclo)alkyl carbonyl or R is H, alkyl or aryl;

$R^1$ is H, alkyl or aryl;

$R^2$ is H, alkyl, aryl or O;

$R^3$ and $R^4$ are independently H, alkyl or aryl and n is an integer from 1 to 10;

or a pharmaceutically acceptable salt, ester or prodrug thereof.

Certain compounds according to the present invention may be conveniently prepared from the appropriate substituted or unsubstituted cyclopropane carbonyl chloride or cyclobutane carbonyl chloride according to the following reaction scheme:

wherein W, Cyc, and p are as defined in connection with Formula (I), Y is O such that R'YH is an alcohol and R' is where $R^1$, $R^2$, X, Z and n are as defined in connection with Formula (Ia).

Other compounds of Formula (I) may be prepared by methods similar to those described in Example 23 and using the appropriate starting materials.

Suitable solvents include inert organic solvents such as dichloromethane and suitable base catalysts include triethylamine and pyridine.

Reaction conditions may be varied depending on the starting materials and the desired end product. Optimization of the reaction conditions would be apparent for one of ordinary skill.

Preferred compounds have unsubstituted cycloalkyl rings (p is 0).

According to a preferred embodiment Y is O, and X is NR or O, n is 1 to 4, p is 0, $R^1$, $R^2$, $R^3$ and $R^4$ are hydrogen, and Z is lower alkyl, cycloalkyl or phenyl; or Y is NR, and X is O, n is 1 or 2, p is 0, $R^1$, $R^2$, $R^3$ and $R^4$ are hydrogen, and Z is hydrogen.

The compounds according to the present invention are exemplified by the following compounds:

cyclopropanecarboxylic acid, 2-[2-(2-methoxy-ethoxy)-ethoxy]-ethyl ester;

cyclobutanecarboxylic acid, 2-[2-(2-methoxy-ethoxy)-ethoxy]-ethyl ester;

(cyclobutanecarbonyl-amino)-acetic acid;

cyclopropanecarboxylic acid 2-(2-benzyloxy-ethoxy)-ethyl ester;

2-(cyclopropanecarbonyl-amino)-propionic acid;

cyclobutanecarboxylic acid 2-(2-benzyloxy-ethoxy)-ethyl ester;

cyclobutanecarboxylic acid, 2-(2-butoxy-ethoxy)-ethyl ester;

cyclobutanecarboxylic acid, 2-(2-ethoxy-ethoxy)-ethyl ester;

cyclopropanecarboxylic acid 2-(2-dimethylamino-ethoxy)-ethyl ester;

cyclobutanecarboxylic acid 2-(2-dimethylamino-ethoxy)-ethyl ester;

cyclopropanecarboxylic acid 2-(2-hexyloxy-ethoxy)-ethyl ester;

cyclobutanecarboxylic acid 2-(2-hexyloxy-ethoxy)-ethyl ester;

cyclopropanecarboxylic acid 2-(2-methoxy-ethoxy)-ethyl ester;

cyclobutanecarboxylic acid 2-(2-methoxy-ethoxy)-ethyl ester;

cyclopropanecarboxylic acid 2-ethoxy-ethyl ester;

cyclobutanecarboxylic acid 2-ethoxy-ethyl ester;

cyclopropanecarboxylic acid 2-isopropoxy-ethyl ester;

cyclobutanecarboxylic acid 2-isopropoxy-ethyl ester;

cyclopropanecarboxylic acid, 2-(2-cyclopropanecarbonyloxy-ethoxy)-ethyl ester;

cyclobutanecarboxylic acid, 2-(2-cyclobutanecarbonyloxy-ethoxy)-ethyl ester;

cyclopropanecarboxylic acid, 2-[2-(2-cyclopropanecarbonyloxy-ethoxy)-ethoxy]-ethyl ester; and cyclobutanecarboxylic acid, 2-[2-(2-cyclobutanecarbonyloxy-ethoxy)-ethoxy]-ethyl ester.

The invention further provides a method for increasing the rate of glucose oxidation and improving glucose utilization in myocardial and other cells, tissue or organs of humans and animals. It has been discovered that substituted or unsubstituted cyclopropanecarboxylic acid and cyclobutanecarboxylic acid, cyclopropanecarboxylic acid and cyclobutanecarboxylic acid represented by the Formula (II) and cyclopropanecarboxylic acid and cyclobutanecarboxylic acid derivatives, such as cyclopropanecarboxylic acid, 2-[2-(2-methoxy-ethoxy)-ethoxy]-ethyl ester and cyclobutanecarboxylic acid, 2-[2-(2-methoxy-ethoxy)-ethoxy]-ethyl ester and other compounds represented by the Formula (I) can increase glucose utilization in myocardial an other types of cells, tissue or organs of warm blooded animals, including humans.

Compounds of Formula II have the structure:

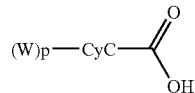

Formula (II)

Wherein
W is $C_1$–$C_6$ alkyl, halogen, or aryl;
Cyc is $C_3$ or $C_4$ cycloalkyl; and
p is an integer from 0 to 3 when Cyc is $C_4$ cycloalkyl, or p is an integer from 0 to 2 when Cyc is $C_3$ cycloalkyl;

According to one embodiment, the method according to the present invention comprises treating cells, tissue or organs of an animal with at least one compound represented by Formula (I) or Formula (II) in an amount effective to stimulate glucose utilization. The compounds of the Formula (I) or Formula (II) may be delivered to the cells, tissues or organs by conventional means of administrating pharmaceutical compositions such as oral administration, injection or infusion, etc., of the compounds of the Formula (I) or (II) to the animal.

The invention further provides pharmaceutical compositions comprising, as its active component, at least one compound according to the Formulas (I) or (II) or their pharmaceutically acceptable salts, esters or prodrugs. Pharmaceutical compositions comprising more than one compound according to the Formulas (I) or (II), their various mixtures and combinations are also contemplated to be within the scope of the present invention.

Pharmaceutical compositions or formulations include compositions and formulations conventionally used in the pharmaceutical arts and may comprise carriers and excipients compatible with oral, intravenous, intramuscular, intraarterial, intracranial, and/or intracavity administration. Suitable pharmaceutical compositions and/or formulations may further compose colloidal dispersion systems, or lipid formulations (e.g., cationic or anionic lipids), micelles, microbeads, etc.

As noted, pharmaceutical compositions of the present invention may comprise pharmaceutically acceptable and physiologically acceptable carriers, diluents or excipients. Examples of suitable carriers, diluents and excipients include solvents (aqueous or non-aqueous), solutions, emulsions, dispersion media, coatings, isotonic and absorption promoting or delaying agents, compatible with pharmaceutical administration, and other commonly used carriers known in the art.

Pharmaceutical compositions may also include carriers to protect the composition against rapid degradation or elimination from the body, and, thus may comprise a controlled release formulation, including implants and microencapsulated delivery systems. For example, a time delay material such as glyceryl monostearate or glyceryl stearate alone, or in combination with a wax, may be employed.

Pharmaceutical compositions can be formulated to be compatible with a particular route of administration. For oral administration, a composition can be incorporated with excipients and used in the form of tablets, pills or capsules, e.g., gelatin capsules. Pharmaceutically compatible binding agents, and/or adjuvant materials can be included in oral formulations. The tablets, pills, capsules, etc., can contain any of the following ingredients, or similar compounds: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; or a flavoring or sweetening agent.

Pharmaceutical compositions for parenteral, intradermal, or subcutaneous administration can include a sterile diluent, such as water, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose.

Pharmaceutical compositions for injection include sterile aqueous solutions (where water-soluble) or dispersions and sterile powders for the extemporaneous preparation of sterile injectable solutions or dispersion. For intravenous administration, suitable carriers include physiological saline, bacteriostatic water, Cremophor E™ (BASF, Parsippany, N.J.) or phosphate buffered saline (PBS). Antibacterial and antifungal agents include, for example, parabens, chlorobutanol, phenol, ascorbic acid and thimerosal. Isotonic agents, for example, sugars, polyalcohols such as manitol, sorbitol, sodium chloride may be included in the composition. Including an agent which delays absorption, for example, aluminum monostearate and gelatin can prolong absorption of injectable compositions.

The pharmaceutical formulations can be packaged in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the pharmaceutical carrier or excipient.

The compositions can be administered by any route compatible with a desired outcome. Thus, routes of administration include oral (e.g., ingestion or inhalation), intraperitoneal, intradermal, subcutaneous, intravenous, intraarterial, intracavity, intracranial, and parenteral. The compositions can also be administered using implants and microencapsulated delivery systems.

Compositions, including pharmaceutical formulations can further include particles or a polymeric substance, such as polyesters, polyamine acids, hydrogel, polyvinyl pyrrolidone, ethylene-vinylacetate, methylcellulose, carboxymethylcellulose, protamine sulfate, or lactide/glycolide copolymers, polylactide/glycolide copolymers, or ethylenevinylacetate copolymers. Cyclopropanecarboxylic acid, cyclopropanecarboxylic acid and derivatives and modified forms thereof can be entrapped in microcapsules, for example, by the use of hydroxymethylcellulose or gelatin-microcapsules, or poly (methylmethacrolate) microcapsules, respectively, or in a colloid drug delivery system.

In instances where cell, tissue or organ targeting is desired, a composition of the invention can of course be delivered to the target cell, organ or tissue by injection or infusion or the like. Targeting can be achieved by injection or infusion in practicing the methods of the invention. Targeting can also be achieved by using proteins that bind to a cell surface protein (e.g., receptor or matrix protein) present on the cell or population of cell types. For example, antibodies or antibody fragments (e.g., Fab region) that bind to a cell surface protein can be included in the delivery systems in order to facilitate cell, tissue or organ targeting. Viral coat proteins that bind particular cell surface proteins can be used for targeting. For example, naturally occurring or synthetic (e.g. recombinant) retroviral envelope proteins with known cell surface protein binding specificity can be employed in the liposomes in order to intracytoplasmically deliver cyclopropanecarboxylic acid, cyclopropanecarboxylic acid and derivatives and modified forms thereof into target cells, tissue or organs. Thus, delivery vehicles, including colloidal dispersion systems, can be made to have a protein coat in order to facilitate targeting or intracytoplasmic delivery of cyclopropanecarboxylic acid, cyclopropanecarboxylic acid and derivatives and modified forms thereof.

The invention further provides a method for prophylactic and therapeutic treatments of various physiological condition or disorder treatable by increasing or improving glucose utilization in cells, tissue or organs of a patient by administering to the patient in need of such treatment, effective amounts of pharmaceutical compositions comprising substituted or unsubstituted cyclopropanecarboxylic acid, cyclopropanecarboxylic acid and cyclobutanecarboxylic acid derivative compounds represented by the Formulas (I) and (II).

Disorders or conditions that can be treated with a method according to the present invention include, for example, ischemic/reperfusion injury, post myocardial infarction, angina, heart failure, a cardiomyopathy, peripheral vascular disease, diabetes, and lactic acidosis, or symptoms or side effects associated with heart surgery (e.g., open heart surgery, bypass surgery, heart transplant).

The method according to the present invention includes administering a pharmaceutical compositions comprising effective amounts of substituted or unsubstituted cyclopropanecarboxylic acid, cyclopropanecarboxylic acid and cyclobutanecarboxylic acid derivative compounds represented by the Formulas (I) and (II) in a single daily dose, or the total daily dosage may be administered in divided doses several times daily. Furthermore, the pharmaceutical compositions may be administered as a single dose or over a period of time.

Patients that can be treated with the method according to the present invention include all known kind of mammals, including non human primates (apes, gibbons, chimpanzees, orangutans, macaques), companion animals (dogs and cats), farm animals (horses, cows, goats, sheep, pigs), experimental animals (mouse, rat, rabbit, guinea pig), and humans.

The dosage regiment utilizing the pharmaceutical compositions according to the present invention is selected based on various factors such as type of physiological condition to be treated, age, weight, sex of the patient, severity of the conditions to be treated, the route of administration, and particular compound contained in the pharmaceutical composition. A physician or veterinarian of ordinary skill can readily determine and prescribed the effective amount of the pharmaceutical composition to prevent or to treat the specific physiological condition.

The daily dosage may be varied over wide range and can be such that the amount of the active compound selected from substituted or unsubstituted cyclopropanecarboxylic acid, cyclopropanecarboxylic acid and cyclobutanecarboxylic acid derivative compounds represented by the Formulas (I) and/or Formula (II) is sufficient to increase glucose utilizationin a cell, tissue or organ of a warm blooded animal and to achieve the desired effect of alleviating or preventing fatty acid-induced ischemic damage.

The invention provides kits containing substituted or unsubstituted cyclopropanecarboxylic acid, cyclopropanecarboxylic acid and derivatives and modified forms thereof represented by the Formulas (I) and Formula (II), including pharmaceutical formulations, packaged into a suitable set. A kit typically includes a label or packaging insert including instructions for use, in vitro, in vivo, or ex vivo, of the components therein.

The term "packaging material" refers to a physical structure housing the components of the kit, such as cyclopropanecarboxylic acid, cyclopropanecarboxylic acid or derivatives or modified forms thereof. The packaging material can maintain the components sterilely, and can be made of material commonly used for such purposes (e.g., paper, corrugated fiber, glass, plastic, foil, ampules, etc.). The label or packaging insert can include appropriate written instructions, for example, practicing a method of the invention.

Kits of the invention therefore can additionally include instructions for using the kit components in a method of the invention. Instructions can include instructions for practicing any of the methods of the invention described herein. Thus, for example, a kit can include a cyclopropanecarboxylic acid, cyclopropanecarboxylic acid or a derivative or modified form thereof in a pharmaceutical formulation in a container, pack, or dispenser together with instructions for administration to a human subject. Instructions may additionally include indications of a satisfactory clinical endpoint or any adverse symptoms that may occur, or any additional information required by the Food and Drug Administration for use in humans.

A kit may include instructions for increasing or improving glucose utilization in vitro, ex vivo or in vivo. In other embodiments, a kit includes instructions for treating instructions for treating a subject having or at risk of having ischemic/reperfusion injury, post myocardial infarction, angina, heart failure, a cardiomyopathy, peripheral vascular disease, diabetes, or lactic acidosis. In another aspect, the instructions comprise instructions for treating a subject having or at risk of having heart surgery (e.g., open heart surgery, bypass surgery, heart transplant and angioplasty).

The instructions may be on "printed matter," e.g., on paper or cardboard within the kit, or on a label affixed to the kit or packaging material, or attached to a vial or tube containing a component of the kit. Instructions may additionally be included on a computer readable medium, such as a disk (floppy diskette or hard disk), optical CD such as CD- or DVD-ROM/RAM, magnetic tape, electrical storage media such as RAM and ROM and hybrids of these such as magnetic/optical storage media.

Kits can additionally include a buffering agent, a preservative, or a stabilizing agent. Each component of the kit can be enclosed within an individual container and all of the various containers can be within a single package.

The present invention is further illustrated in the following examples wherein all parts, percentages, and ratios are in equivalents, all temperatures are in ° C., and all pressures are atmospheric unless otherwise indicated:

EXAMPLES

Example 1

Preparation of Cyclopropanecarboxylic acid, 2-[2-(2-methoxy-ethoxy)-ethoxy]-ethyl ester

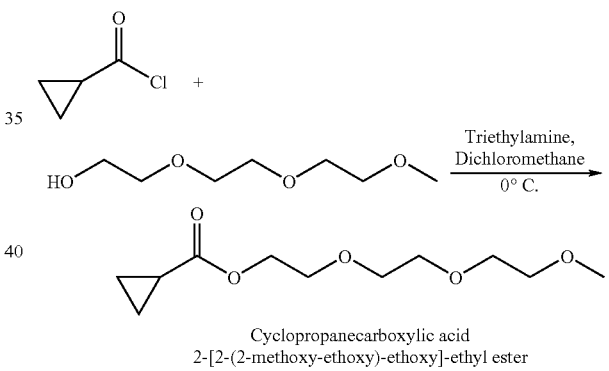

Triethylene glycol monomethyl ether (1.1 eq, 5.26 mmol, 0.84 ml) and triethylamine (1.1 eq, 5.26 mmol, 0.73 ml) were taken in a 10 ml round bottom flask and dichloromethane (3 ml) was added. This mixture was cooled to 0° C. and then cyclopropanecarbonyl chloride (4.78 mmol, 0.5 g, 0.43 ml) was added in a dropwise fashion maintaining the temperature at 0° C. with constant stirring.

A yellowish-orange solid was observed after some time. Stirring was continued for 1 hour at 0° C. The reaction was monitored by thin layer chromatography, and then quenched with saturated ammonium chloride solution. The mixture was then transferred to a separatory funnel, washed with 5% sodium bicarbonate (2×5 ml), 1:1 hydrochloric acid (2×5 ml) and then with brine (5 ml). The dichloromethane layer was separated from the aqueous layer, dried over anhydrous sodium sulphate, filtered, and evaporated in vacuo to give the title product as a pale yellow liquid. Purification was by flash chromatography and vacuum distillation (b.p.=144° C., 3.0 mm of Hg) which afforded the pure product as a colorless liquid (527.0 mg, 48%).

The compound obtained was characterized by $^1H$ and $^{13}C$ NMR, IR, and mass spectroscopy:

$^1H$ NMR (300 MHz, CDCl$_3$) δ 4.2 (m, 2H), 3.68 (m, 2H), 3.64 (m, 6H), 3.52 (m, 2H), 3.36 (s, 3H), 1.62 (m, 1H), 0.99 (m, 2H), 0.84 (m, 2H); IR (CHCl$_3$) 2876.07, 1726.62, 1199.53, 1179.49, 1107.97 cm$^{-1}$; $^{13}C$ NMR (75.5 MHz, CDCl$_3$) δ 174.67, 71.80, 70.44, 69.06, 63.45, 58.84, 12.65, 8.35; MS (ES, MNa$^+$): calculated for C$_{11}$H$_{20}$O$_5$Na 255.11, found 255.1.

Example 2

Preparation of Cyclobutanoylglycine (Cyclobutanecarbonyl-amino)-acetic acid)

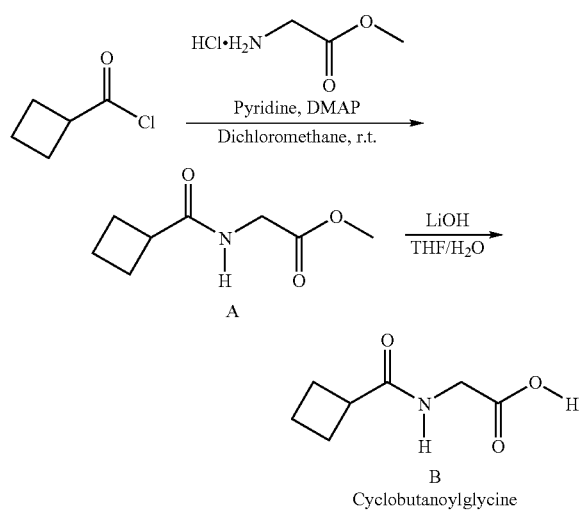

Methyl ester glycine hydrochloride (1 eq, 2.39 mmol, 300 mg) and pyridine (2 eq, 4.78 mmol, 0.39 ml) were suspended in (5 ml) of dichloromethane followed by addition of DMAP (1.5 eq, 218.5 mg) in one portion; the reaction mixture was stirred for 30 minutes at room temperature. After 30 minutes, cyclobutanecarbonyl chloride (2 eq, 4.77 mmol, 0.54 ml) was added slowly and the reaction mixture was stirred for 4 hours at room temperature. The solvent was evaporated in vacuo and the residue extracted with ethyl acetate. The ethyl acetate layer was dried and concentrated to dryness. The crude material obtained was purified by flash chromatography to yield pure compound A (358 mg, 87%).

To a solution of A in (6 ml) THF, was added lithium hydroxide (1.1 eq, 2.3 mmol, 2.3 ml, 1M) at room temperature and the reaction mixture was stirred for 1.5 hours. The reaction mixture was then concentrated in vacuo and acidified to pH=3 with 2N HCl. The crude product was then extracted with ethyl acetate and purified by recrystallization, using an ethyl acetate/hexane mixture. The product obtained after recrystallization was further purified by flash chromatography and again recrystallization to give the title compound B as a white solid (196 mg, 59%).

The compound obtained was characterized by $^1H$ and $^{13}C$ NMR, IR, and mass spectroscopy:

$^1$HNMR (300 MHz, CD$_3$OD) δ 3.87 (s, 2H), 3.14 (quintet, 1H), 1.84–2.2 (m, 6H); IR (USCOPE) 3313.01, 3098.14, 2986.18, 2940.41, 2525.15, 2469.13, 2435.25, 1738.49, 1620.96, 1566.87, 1486.61, 1346.65, 1264.23 cm$^{-1}$; $^{13}C$ NMR (75.5 MHz, CD$_3$OD) δ 178.20, 173.12, 41.69, 40.61, 26.12, 19.01; HRMS (ES, MNa$^+$): calculated for C$_7$H$_{11}$NO$_3$Na 180.06311, found 180.06290.

Example 3

Preparation of Cyclobutanecarboxylic acid, 2-[2-(2-methoxy-ethoxy)-ethoxy]-ethyl ester

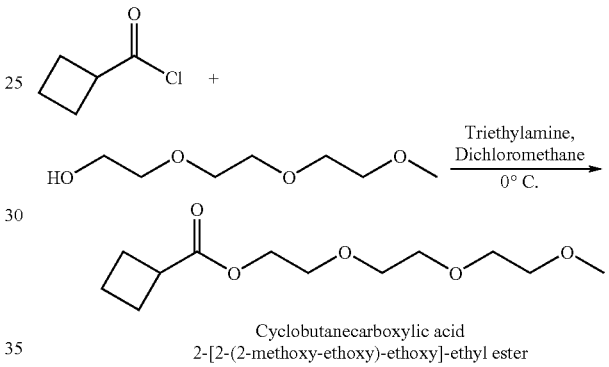

Cyclobutanecarboxylic acid 2-[2-(2-methoxy-ethoxy)-ethoxy]-ethyl ester

Triethylene glycol monomethyl ether (1.1 eq, 4.64 mmol, 0.74 ml) and triethylamine (1.1 eq, 4.64 mmol, 0.65 ml) were taken in a 25 ml round bottom flask and dichloromethane (3 ml) was added. This mixture was cooled to 0° C. and then cyclobutanecarbonyl chloride (4.22 mmol, 0.5 g, 0.48 ml) was added in a dropwise fashion maintaining the temperature at 0° C. with constant stirring (vigorous reaction).

A pink colored solution was observed after some time. An extra 4 ml of dichoromethane was added to maintain proper stirring (the reaction mixture became thick). Stirring was continued for 1 hour at 0° C. The reaction was monitored by thin layer chromatography and then quenched with saturated ammonium chloride solution. The mixture was then transferred to a separatory funnel, washed with 5% sodium bicarbonate (2×5 ml), 1:1 hydrochloric acid (2×5 ml) and then with brine (5 ml). The dichloromethane layer was separated from the aqueous layer, dried over anhydrous sodium sulphate, filtered, and evaporated in vacuo to give the title product as a pale yellowish-pink liquid. The liquid was purified by flash chromatography and vacuum distillation (b.p.=189° C., 3.0 mm of Hg) to yield the pure product as a colorless liquid (679.6 mg, 65.34%).

The product was characterized by 1H and $^{13}C$ NMR, IR and mass spectroscopy:

$^1$HNMR (300 MHz, CDCl$_3$) δ 4.18 (m, 2H), 3.4 (m, 2H), 3.6 (m, 6H), 3.5 (m, 2H), 3.32 (s, 3H), 3.1 (quintet, 1H), 2.2 (m, 4H), 1.86 (m, 2H); IR (CDCl$_3$) 2946.38, 2870.68, 1730.73, 1179.35, 1109.59 cm$^{-1}$; $^{13}$C NMR (75.5 MHz, CDCl$_3$) δ 175.45, 71.93, 70.58, 69.21, 63.40, 59.01, 38.0, 25.24, 18.38; MS (ES, MNa$^+$): calculated for C$_{12}$H$_{22}$O$_5$Na 269.13, found 269.1.

Examples 4, 6 to 14, 18 and 19

General Procedure for the Preparation of Certain Cyclopropanecarboxylic Acid and Cyclobutanecarboxylic Acid Derivatives

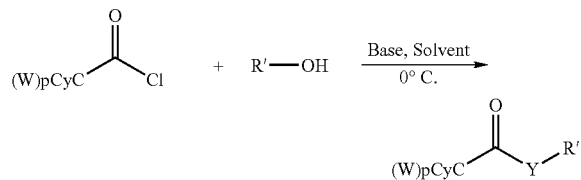

where W, Cyc, and p are as defined for Formula (I) and Y is O such that R'—YH is an alcohol, where R' is:

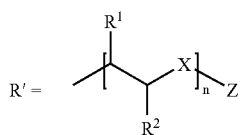

where R$^1$, R$^2$, Z and n are defined in connection with Formula (Ia); using triethylamine or pyridine as a base and dichloromethane as a solvent.

Following the procedures described in Example 1 and Example 3 and using the appropriate starting alcohol and cycloalkyl cyclopropane carboxylic acid chloride materials, (the appropriate starting alcohols were used in place of triethylene glycol monomethyl ether), the noted cyclopropanecarboxylic acid and of cyclobutanecarboxylic acid derivatives respectively were prepared (see Table I). The compounds prepared, cycloalkyl carbonylchloride and alcohol starting materials used for their preparation and their molecular weights are summarized in Table 1.

The compounds were characterized by $^1$H NMR, $^{13}$C NMR, IR and mass spectroscopy.

Example 5

Preparation of Cyclopropanoylalanine

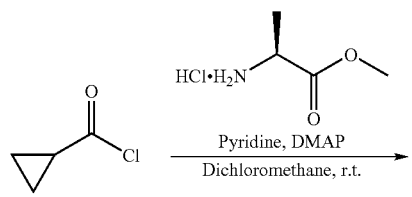

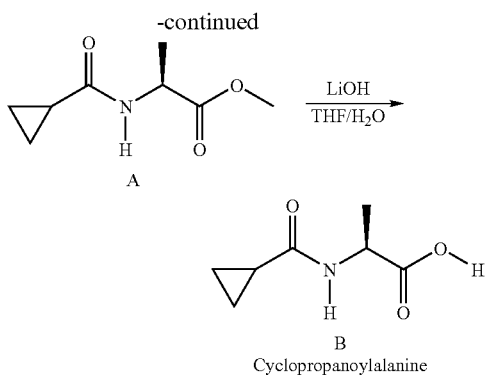

Cyclopropanoylalanine

The procedure of Example 2 was followed except that 2.5 equivalents of pyridine was used instead of 2 equivalents, cyclopropanecarbonyl chloride was used in place of cyclobutanecarbonylchloride and methyl ester alanine hydrochloride was used in place of methyl ester glycine hydrochloride.

Purified compound B (321 mg, 87%) was characterized by $^1$H and $^{13}$C NMR, IR, and mass spectroscopy.

$^1$HNMR (300 MHz, CD$_3$OD) δ 8.25 (br s, 1H), 4.38 (m, 1H), 3.25 (s, 1H), 1.64 (m, 1H), 1.39 (dd, 3H), 0.7–0.9 (m, 4H); IR-(USCOPE) 3323.78, 3020.25, 2645.76, 1791.56, 1729.13, 1632.33, 1537.27, 1406.24, 1281.02 cm$^{-1}$; $^{13}$C NMR (75.5 MHz, CD$_3$ OD) δ 176.28, 176.18, 49.38, 17.77, 14.59, 7.41, 7.33; HRMS (ES, M): calculated for C$_7$H$_{12}$NO$_3$ 158.08117, found 158.08123.

Example 15

Preparation of Cyclopropanecarboxylic acid 2-ethoxy-ethyl ester

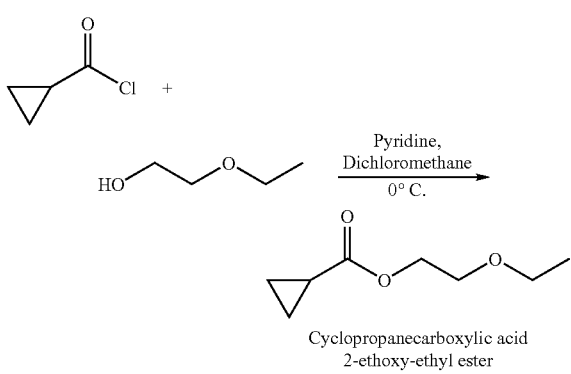

Cyclopropanecarboxylic acid 2-ethoxy-ethyl ester

2-Ethoxy-ethanol (1.1 eq, 5.26 mmol, 0.47 g, 0.51 ml) and pyridine (1.1 eq, 5.26 mmol, 0.42 g, 0.43 ml) were taken in a 25 ml round bottom flask and dichloromethane (6 ml) was added. This mixture was cooled to 0° C. and then cyclopropanecarbonyl chloride (4.78 mmol, 0.5 g, 0.43 ml) was added in a dropwise fashion maintaining the temperature at 0° C. with constant stirring.

An orange-yellow colored solution was observed after sometime. Stirring was continued for 1 hour at 0° C. The reaction was monitored by thin layer chromatography and then quenched with saturated ammonium chloride solution. The mixture was then transferred to a separatory funnel, washed with 5% sodium bicarbonate (2×5 ml), 1:1 hydrochloric acid (2×5 ml), and then with brine (5 ml). The dichloromethane layer was separated from the aqueous layer, dried over anhydrous magnesium sulphate, filtered, and evaporated in vacuo to give the title product as a pale yellowish-orange liquid. Purification was by flash chromatography and vacuum distillation (b.p.=43° C., 2.8 mm of Hg) which afforded the pure product as a colorless liquid (515.8 mg, 55.4%).

Characterization was done by NMR ($^1$H and $^{13}$C), IR, and mass spectroscopy:

$^1$HNMR (400 MHz, CDCl$_3$) δ 4.22 (m, 2H), 3.62 (m, 2H), 3.53 (q, 2H), 1.64 (m, 1H), 1.2 (t, 3H), 0.98 (m, 2H), 0.84 (m, 2H); MS (ES, M+Na): calculated for C$_8$H$_{14}$O$_3$Na 181.19, found 181.1; IR (CH$_2$Cl$_2$) 2976.37, 2869.55, 1728.78, 1455.55, 1177.86 cm$^{-1}$; $^{13}$CNMR (125 MHz, CDCl$_3$) δ 174.76, 68.39, 66.60, 63.73, 15.17, 12.91, 8.62.

Example 16

Preparation of Cyclobutanecarboxylic acid 2-ethoxy-ethyl ester

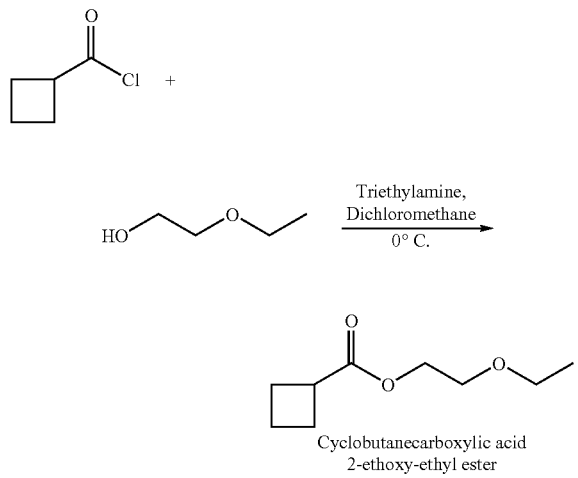

Cyclobutanecarboxylic acid 2-ethoxy-ethyl ester

2-Ethoxy-ethanol (1.1 eq, 4.64 mmol, 0.42 g, 0.45 ml) and triethylamine (1.1 eq, 4.64 mmol, 0.47 g, 0.65 ml) were taken in a 25 ml round bottom flask and dichloromethane (6 ml) was added. This mixture was cooled to 0° C. and then cyclobutanecarbonyl chloride (4.22 mmol, 0.5 g, 0.48 ml) was added in a dropwise fashion maintaining the temperature at 0° C. with constant stirring.

An orange-yellow colored solution was observed after sometime. Stirring was continued for 1 hour at 0° C. The reaction was monitored by thin layer chromatography and then quenched with saturated ammonium chloride solution. The mixture was then transferred to a separatory funnel; washed with 5% sodium bicarbonate (2×5 ml), 1:1 hydrochloric acid (2×5 ml), and then with brine (5 ml). The dichloromethane layer was separated from the aqueous layer, dried over anhydrous magnesium sulphate, filtered, and evaporated in vacuo to give the title product as a pale yellow liquid. Purification was attempted by flash chromatography and vacuum distillation (b.p.=48° C., 2.8 mm of Hg) which afforded the pure product as a colorless liquid (421.3 mg, 57.7%).

Characterization was done by NMR ($^1$H and $^{13}$C), IR, and mass spectroscopy:

$^1$HNMR (500 MHz, CDCl$_3$) δ 4.18 (m, 2H), 3.58 (m, 2H), 3.48 (q, 2H), 3.14 (m, 1H) 2.2 (m, 4H), 1.9 (m, 2H), 1.17 (t, 3H); MS (ES, M+Na): calculated for C$_9$H$_{16}$O$_3$Na 195.11, found 195.1; IR (CH$_2$Cl$_2$) 2976.99, 2949.17, 1732.12, 1444.39, 1175.39 cm$^{-1}$; $^{13}$CNMR (125 MHz, CDCl$_3$) δ 175.33, 68.38, 66.58, 63.51, 38.06, 25.32, 18.47, 15.16.

Example 17

Preparation of Cyclopropanecarboxylic acid 2-isopropoxy-ethyl ester

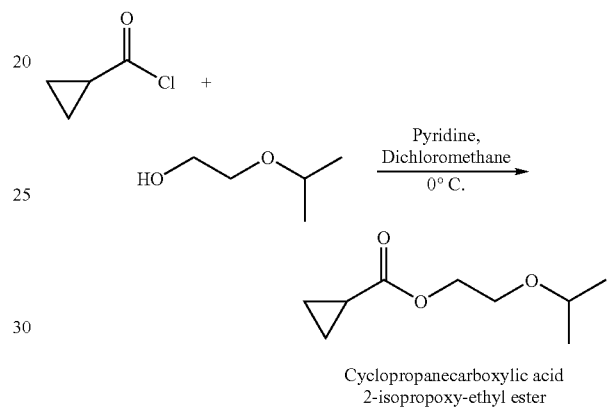

Cyclopropanecarboxylic acid 2-isopropoxy-ethyl ester

2-Isopropoxy-ethanol (1.1 eq, 5.26 mmol 0.55 g, 0.61 ml) and pyridine (1.1 eq, 5.26 mmol, 0.42 g, 0.43 ml) were taken in a 25 ml round bottom flask and dichloromethane (6 ml) was added. This mixture was cooled to 0° C. and then cyclopropanecarbonyl chloride (4.78 mmol, 0.5 g, 0.43 ml) was added in a dropwise fashion maintaining the temperature at 0° C. with constant stirring.

An orange-yellow colored solution was observed after sometime. An extra 2 ml of dichoromethane was added to maintain proper stirring (reaction mixture becomes thick). Stirring was continued for 1 hour at 0° C. The reaction was monitored by thin layer chromatography and then quenched with saturated ammonium chloride solution. The mixture was then transferred to a separatory funnel, washed with 5% sodium bicarbonate (2×5 ml), 1:1 hydrochloric acid (2×5 ml), and then with brine (5 ml). The dichloromethane layer was separated from the aqueous layer, dried over anhydrous magnesium sulphate, filtered, and evaporated in vacuo to give the title product as a pale yellowish-orange liquid. Purification was by flash chromatography and vacuum distillation (b.p.=33° C., 2.9 mm of Hg) which afforded the pure product as a colorless liquid (630.2 mg, 76.40%).

Characterization of the resulting compound was done by $^1$H and $^{13}$C NMR, IR, and mass spectroscopy:

$^1$HNMR (400 MHz, CDCl$_3$) δ 4.2 (m, 2H), 3.6 (m, 3H), 1.65 (m, 1H), 1.15 (d, 6H), 1.0 (m, 2H), 0.85 (m, 2H); IR (CH$_2$Cl$_2$) 3015.93, 2972.88, 1729.05, 1454.97, 1177.85 cm$^{-1}$; $^{13}$C NMR (125 MHz, CDCl$_3$) δ 174.72, 71.93, 65.95, 64.0, 22.06, 12.92, 8.54; MS (ES, MNa$^+$): calculated for C$_9$H$_{16}$O$_3$Na 195.09, found 195.0.

Example 20

Preparation of Cyclobutanecarboxylic acid, 2-(2-cyclobutanecarbonyloxy-ethoxy)-ethyl ester

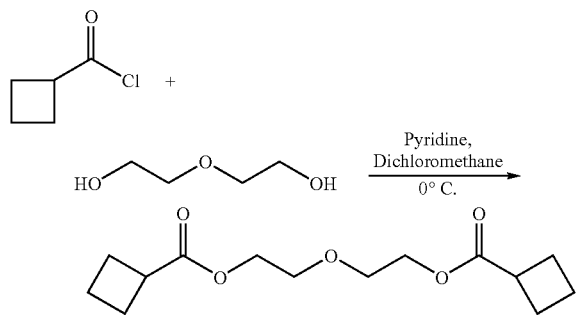

Diethylene glycol (0.5 eq, 1 mmol, 0.11 g) and pyridine (2.2 eq, 2.2 mmol, 0.174 g, 0.18 ml) were taken in a 10 ml round bottom flask and dichloromethane (4 ml) was added. This mixture was cooled to 0° C. and then cyclobutanecarbonyl chloride (2.0 mmol, 0.24 g, 0.23 ml) was added in a dropwise fashion maintaining the temperature at 0° C. with constant stirring.

A white thick suspension was observed after sometime. Stirring was continued for 1 hour at 0° C. The reaction was monitored by thin layer chromatography and then quenched with saturated ammonium chloride solution. The mixture was then transferred to a separatory funnel, washed with 5% sodium bicarbonate (2×5 ml), 1:1 hydrochloric acid (2×5 ml), and then with brine (5 ml). The dichloromethane layer was separated from the aqueous layer, dried over anhydrous magnesium sulphate, filtered, and evaporated in vacuo to give the title product as a pale yellowish liquid. Purification was by flash chromatography and vacuum distillation (b.p.=113° C., 2.8 mm of Hg) which afforded the pure product as a colorless liquid (130.0 mg, 46.42%)

Characterization was done by NMR ($^1$H and $^{13}$C), IR, and mass spectroscopy:

$^1$HNMR (500 MHz, CDCl$_3$) δ 4.2 (m, 4H), 3.63 (m, 4H), 3.14(m, 2H), 1.9–2.2(m, 12H); MS (ES, M+Na): calculated for C$_{14}$H$_{22}$O$_5$Na 293.15, found 293.0; IR (CH$_2$Cl$_2$) 2949.36, 2869.67, 1731.42, 1445.39, 1174.72 cm$^{-1}$; $^{13}$CNMR (125 MHz, CDCl$_3$) δ 175.26, 69.16, 63.32, 63.27, 38.05, 25.33, 18.49.

Example 21

Preparation of Cyclopropanecarboxylic acid, 2-[2-(2-cyclopropanecarbonyloxy-ethoxy)-ethoxy]-ethyl ester

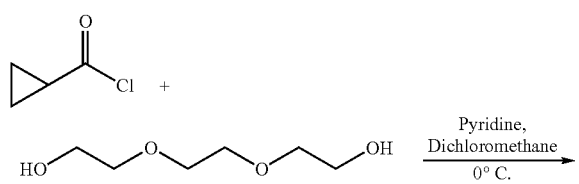

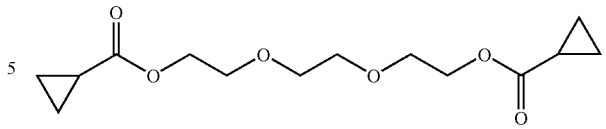

Triethylene glycol (1.6 mmol, 0.24 g) and pyridine (2.2 eq, 3.52 mmol, 0.28 g, 0.28 ml) were taken in a 10 ml round bottom flask and dichloromethane (5 ml) was added. This mixture was cooled to 0° C. and then cyclopropanecarbonyl chloride (3.4 mmol, 0.36 g, 0.31 ml) was added in a dropwise fashion maintaining the temperature at 0° C. with constant stirring.

A white, thick suspension was observed after sometime. Stirring was continued for 1 hour at 0° C. The reaction was monitored by thin layer chromatography and then quenched with saturated ammonium chloride solution. The mixture was then transferred to a separatory funnel, washed with 5% sodium bicarbonate (2×5 ml), 1:1 hydrochloric acid (2×5 ml), and then with brine (5 ml). The dichloromethane layer was separated from the aqueous layer, dried over anhydrous magnesium sulphate, filtered, and evaporated in vacuo to give the title product as a pale yellowish liquid. Purification was by flash chromatography and vacuum distillation (b.p.=127° C., 2.8 mm of Hg) which afforded the pure product as a colorless liquid (234.5 mg, 50.97%).

Characterization was done by NMR ($^1$H and $^{13}$C), IR, and mass spectroscopy:

$^1$HNMR (500 MHz, CDCl$_3$) δ 4.2 (m, 4H), 3.68 (m, 4H), 3.64(br s, 4H), 1.62(m, 2H), 0.97 (m,4H), 0.84 (m, 4H); MS (ES, M+Na): calculated for C$_{14}$H$_{22}$O$_6$Na 309.14, found 309.0; IR (CH$_2$Cl$_2$) 3015.01, 2951.60, 2873.12, 1726.69, 1454.28, 1177.84 cm$^{-1}$; $^{13}$CNMR (125 MHz, CDCl$_3$) δ 175.0, 70.0, 69.0, 63.0, 13.0, 8.0.

Example 22

Preparation of Cyclobutanecarboxylic acid, 2-[2-(2-cyclobutanecarbonyloxy-ethoxy)-ethoxy]-ethyl ester

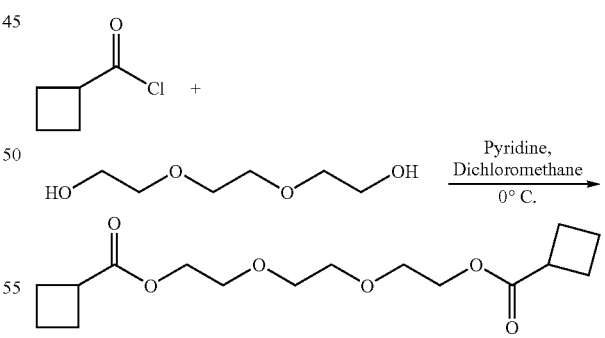

The procedure described in Example 21 was followed using the following amounts of these reagents: triethylene glycol (1.6 mmol, 0.24 g), pyridine (2.2 eq, 3.52 mmol, 0.28 g, 0.28 ml); and cyclobutanecarbonyl chloride (3.4 mmol, 0.40 g, 0.39 ml).

The compound was characterized by NMR ($^1$H and $^{13}$C), IR and mass spectroscopy:

$^1$HNMR (500 MHz, CDCl$_3$) δ 4.2 (m, 4H), 3.68 (m, 4H), 3.62(br s, 4H), 3.14(m, 2H), 2.1–2.3 (m,8H), 1.8–2.0 (m,

4H); MS (ES, M+Na): calculated for $C_{16}H_{26}O_6Na$ 337.14, found 337.0; IR ($CH_2Cl_2$) 2948.71, 2869.27, 1731.17, 1445.80, 1175.60 cm$^{-1}$; $^{13}$CNMR (125 MHz, CDCl$_3$) δ 175.29, 70.59, 69.27, 63.39, 38.06, 25.33, 18.49.

Example 23

Preparation of Cyclopropanecarboxylic acid 2-[{2-[bis(2-cyclopropanecarbonyloxy-ethyl)-amino]-ethyl}-(2-cyclopropanecarbonyloxy-ethyl)-amino] ethyl ester

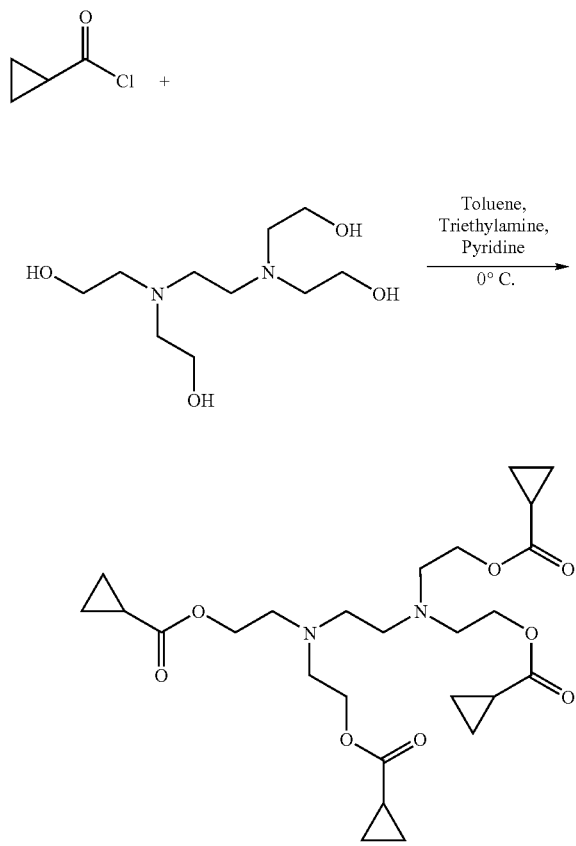

A solution of the diamine tetra-ol (1 eq, 4.23 mmol, 1.0 g), pyridine (1.0 eq, 4.23 mmol, 0.33 g, 0.34 ml) and triethylamine (5.0 eq, 0.021 mol, 2.12 g, 2.90 ml) was taken in a 25 ml round bottom flask and toluene (10 ml) was added. This mixture was cooled to 0° C. and then cyclopropanecarbonyl chloride (0.019 mol, 1.98 g, 1.72 ml) was added in one shot with vigorous stirring, maintaining the temperature at 0° C.

A yellowish-white thick suspension was observed after sometime. Stirring was continued for 15 minutes at 0° C. The reaction was monitored by thin layer chromatography and then quenched with saturated ammonium chloride solution. The mixture was then transferred to a separatory funnel, and extracted with ethyl acetate (2×25 ml). The ethyl acetate layer was washed with brine (1×20 ml), dried over anhydrous magnesium sulphate, filtered, and evaporated in vacuo to give the title product as a pale yellowish liquid. Purification was by flash chromatography which afforded the pure product as a colorless liquid (900.0 mg, 42.0%).

Characterization was done by NMR ($^1$H and $^{13}$C), IR, and mass spectroscopy:

$^1$HNMR (300 MHz, CDCl$_3$) δ 4.13 (t, 8H), 3.3 (m, 3H), 2.82 (t, 8H), 2.68 (s, 4H) 1.64 (m,4H), 0.88 (m, 16H); MS (ES, M+H): calculated for $C_{26}H_{40}N_2O_8$ +H 509.29, found 509.0; IR ($CH_2Cl_2$) 3014.69, 2958.19, 2826.89, 1725.90, 1452.31, 1173.00 cm$^{-1}$; $^{13}$CNMR (125 MHz, CDCl$_3$) δ 174.59, 62.62, 53.55, 53.29, 12.92, 8.50.

Example 24

Preparation of Cyclopropanecarboxylic acid (2-isopropoxy-ethyl)-amide

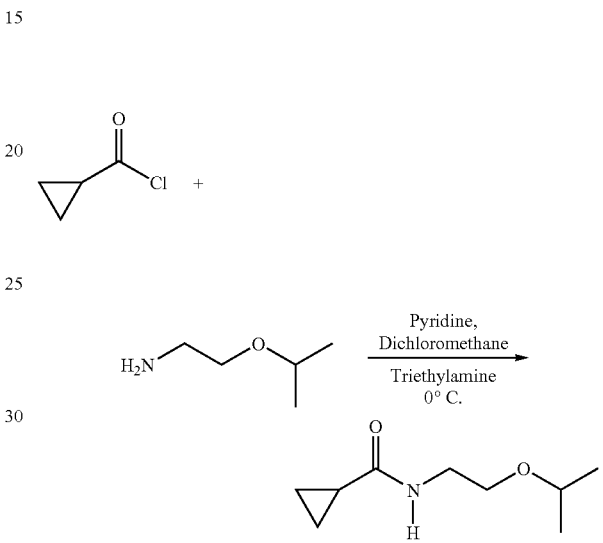

A solution of the amino ether (1.1 eq, 5.26 mmol, 0.54 g, 0.64 ml), pyridine (0.5 eq, 2.39 mmol, 0.19 g, 0.19 ml), triethylamine (1.1 eq, 5.26 mmol, 0.53 g, 0.73 ml) was taken in a 10 ml round bottom flask and dichloromethane (6 ml) was added. This mixture was cooled to 0° C. and then cyclopropanecarbonyl chloride (4.78 mmol, 0.5 g, 0.43 ml) was added in a dropwise fashion, maintaining the temperature at 0° C.

A white precipitate was observed after sometime. Stirring was continued for 30 minutes at 0° C. The reaction was monitored by thin layer chromatography and then quenched with saturated ammonium chloride solution. The mixture was then transferred to a separatory funnel, washed with water (1×10 ml), brine (2×10 ml), dried over anhydrous magnesium sulphate, filtered, and evaporated in vacuo to give the title product as a colorless liquid. Purification was by flash chromatography and vacuum distillation (b.p.=106° C., 1.4 mm of Hg) which afforded the pure product as a colorless liquid (493.8 mg, 60.22%).

Characterization was done by NMR ($^1$H and $^{13}$C), IR, and mass spectroscopy:

$^1$HNMR (300 MHz, CDCl$_3$) δ 6.0 (br s, 1H), 3.57 (m, 1H), 3.44 (m, 4H), 1.32 (m, 1H) 1.14 (d, 6H), 0.94 (m, 2H), 0.7 (m, 2H); MS (EI, M$^+$): calculated for $C_9H_{17}NO_2$ 171.12, found 171.12; IR ($CH_2Cl_2$) 3299.39, 3092.61, 2971.98, 2868.14, 1644.61, 1552.31, 1197.34 cm$^{-1}$; $^{13}$CNMR (125 MHz, CDCl$_3$) δ 173.41, 71.76, 66.68, 39.83, 22.10, 14.72, 7.07.

Example 25

Preparation of
(±)-trans-2-Phenyl-cyclopropanecarboxylic acid
2-isopropoxy-ethyl ester

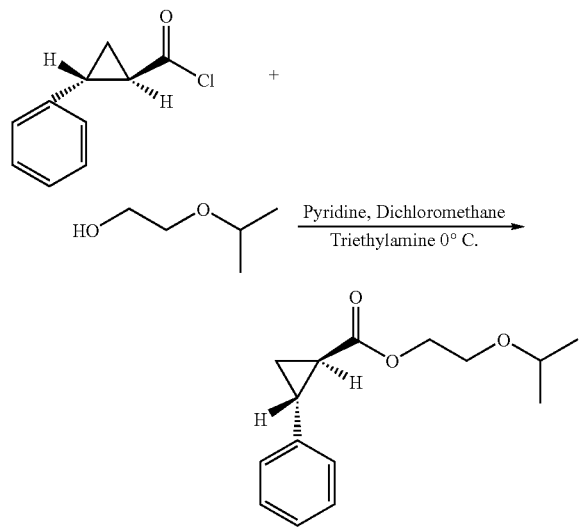

2-Isopropoxy-ethanol (1.1 eq, 3.04 mmol, 0.32 g, 0.35 ml), pyridine (0.5 eq, 1.38 mmol, 0.11 g, 0.11 ml), triethylamine (1.1 eq, 3.04 mmol, 0.31 g, 0.43 ml) were taken in a 10 ml round bottom flask and dichloromethane (6 ml) was added. This mixture was cooled to 0° C. and then (±)-trans-2-phenyl-cyclopropanecarbonyl chloride (2.76 mmol, 0.5 g, 0.43 ml) was added in a dropwise fashion, maintaining the temperature at 0° C.

A white precipitate was observed after sometime. Stirring was continued for 30 minutes at 0° C. The reaction was monitored by thin layer chromatography and then quenched with saturated ammonium chloride solution. The mixture was then transferred to a separatory funnel, washed with 5% sodium bicarbonate (2×5 ml), 1:1 hydrochloric acid (2×5 ml), and then with brine (5 ml). The dichloromethane layer was separated from the aqueous layer, dried over anhydrous magnesium sulphate, filtered, and evaporated in vacuo to give the title product as a pale yellowish liquid. Purification was by flash chromatography which afforded the pure product as a colorless liquid (450.0 mg, 65.0%). The above compound is racemic as determined by chiral HPLC (chiralcel OJ column) 2% Isopropanol in hexane. UV $\lambda_{max}$=278 nm (flow=1 ml/min).

Characterization was done by NMR ($^1$H and $^{13}$C), IR, and mass spectroscopy:

$^1$HNMR (300 MHz, CDCl$_3$) δ 7.07–7.27 (m, 5H), 4.22 (m, 2H), 3.61 (m, 3H), 2.51 (m, 1H) 1.93 (m, 1H), 1.58 (m, 1H), 1.26 (m, 1H), 1.53 (d, 6H); MS (EI, M$^+$): calculated for C$_{15}$H$_{20}$O$_3$ 248.14, found 248.14; IR (CH$_2$Cl$_2$) 3063.09, 3030.28, 2971.95, 2867.20, 1727.02, 1151.71 cm$^{-1}$; $^{13}$CNMR (125 MHz, CDCl$_3$) δ 173.27, 139.92, 128.36, 126.39, 126.10, 72.01, 65.94, 64.33, 26.44, 24.17, 22.10, 17.26.

Example 26

Preparation of
(±)-trans-2-Phenyl-cyclopropanecarboxylic acid
2-ethoxy-ethyl ester

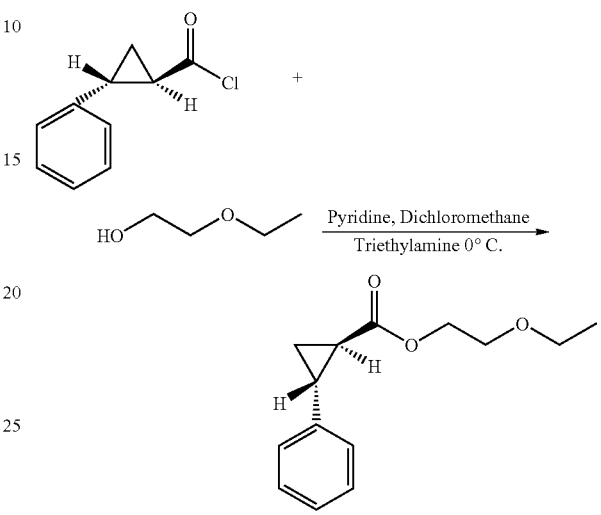

This compound was prepared using the procedure described in Example 25 and using the following reagents:
2-ethoxy-ethanol (1.1 eq, 3.05 mmol, 0.27 g, 0.30 ml) pyridine (0.5 eq, 1.39 mmol, 0.11 g, 0.11 ml), triethylamine (1.1 eq, 3.05 mmol, 0.31 g, 0.43 ml); and (±)-trans-2-phenyl-cyclopropanecarbonyl chloride (2.77 mmol, 0.5 g, 0.43 ml).

The compound was characterized by NMR ($^1$H and $^{13}$C), IR and mass spectroscopy:

$^1$HNMR (300 MHz, CDCl$_3$) δ 7.06–7.28 (m, 5H), 4.24 (m, 2H), 3.62 (m, 2H), 3.52 (q, 2H) 2.51 (m, 1H), 1.94 (m, 1H), 1.58 (m, 1H), 1.29 (m, 1H), 1.19 (t, 3H); MS (EI, M$^+$): calculated for C$_{14}$H$_{18}$O$_3$ 234.12, found 234.12; IR (CH$_2$Cl$_2$) 2975.07, 2868.63, 1726.37, 1175.66 cm$^{-1}$; $^{13}$CNMR (125 MHz, CDCl$_3$) δ 173.26, 139.90, 128.37, 126.40, 126.08, 68.36, 66.65, 64.04, 26.48, 24.13, 17.35, 15.2

Example 27

Preparation of 1-Phenyl-cyclopropanecarboxylic acid 2-ethoxy-ethyl ester

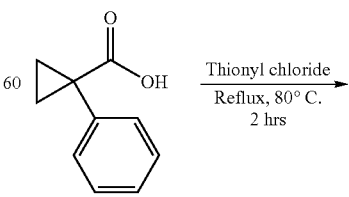

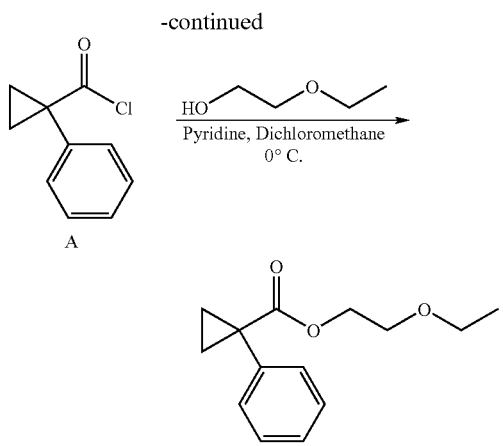

1-Phenyl-cyclopropanecarboxylic acid (0.5 g, 3.1 mmol), was dissolved in thionyl chloride (10 eq, 0.031 mol, 3.68 g, 2.3 ml), and refluxed at 80° C. for 1.5 hours. Then excess of thionyl chloride was evaporated on the rotary evaporator which yielded a dark-yellowish liquid (1-phenyl-cyclopropanecarbonyl chloride A), which was then cooled to 0° C., under argon.

2-Ethoxy-ethanol (1.1 eq, 3.41 mmol, 0.31 g, 0.33 ml) and pyridine (1.2 eq, 3.41 mmol, 0.27 g, 0.28 ml) was taken in a 25 ml round bottom flask and dichloromethane (10 ml) was added. This mixture was cooled to 0° C. and then A was added in a dropwise fashion maintaining the temperature at 0° C. Stirring was continued for 30 minutes at 0° C. The reaction was monitored by thin layer chromatography and then quenched with saturated ammonium chloride solution. The mixture was then transferred to a separatory funnel, washed with 5% sodium bicarbonate (2×5 ml), 1:1 hydrochloric acid (2×5 ml), and then with brine (5 ml). The dichloromethane layer was separated from the aqueous layer, dried over anhydrous magnesium sulphate, filtered, and evaporated in vacuo to give the title product as a pale yellowish liquid. Purification was by flash chromatography and vacuum distillation (b.p.=93° C., 2.4 mm of Hg), which afforded the pure product as a colorless liquid (437.7 mg, 60.62%)

Characterization was done by NMR ($^1$H and $^{13}$C), IR, and mass spectroscopy:

$^1$HNMR (300 MHz, CDCl$_3$) δ 7.2–7.35 (m, 5H), 4.14 (m, 2H), 3.51 (m, 2H), 3.35 (q, 2H) 1.60 (dd, 2H), 1.18 (dd, 2H), 1.1 (t, 3H); MS (EI, M$^+$): calculated for C$_{14}$H$_{18}$O$_3$ 234.12, found 234.12; IR (CH$_2$Cl$_2$) 2958.04, 2837.41, 1676.09, 1600.65, 1288.07 cm$^{-1}$; $^{13}$CNMR (125 MHz, CDCl$_3$) δ 174.28, 139.40, 130.41, 127.97, 127.00, 68.11, 66.57, 64.43, 29.19, 16.59, 15.23.

Note:

For the compounds of Examples 1 to 27, the solvent system used for flash chromatography was ethyl acetate/hexane, unless otherwise specified.

TABLE 1

| Example | Compound | Molecular Weight | Starting Carbonyl Chloride | Starting R'-YH compound |
|---|---|---|---|---|
| 1 MM054 | Cyclopropanecarboxylic acid 2-[2-(2-methoxy-ethoxy)-ethoxy]-ethyl ester | 232.28 | P* | 2-[2-(2-Methoxy-ethoxy)-ethoxy]-ethanol |
| 2 MM055 | (Cyclobutanecarbonyl-amino)-acetic acid | 157.17 | B** | Methyl ester glycine hydrochloride (Amino Acid) |
| 3 MM056 | Cyclobutanecarboxylic acid 2-[2-(2-methoxy-ethoxy)-ethoxy]-ethyl ester | 246.31 | B | 2-[2-(2-Methoxy-ethoxy)-ethoxy]-ethanol |
| 4 MM057 | Cyclopropanecarboxylic acid 2-(2-benzyloxy-ethoxy)-ethyl ester | 264.31 | P | 2-(2-Benzyloxy-ethoxy)-ethanol |

TABLE 1-continued

| Example | Compound | Molecular Weight | Starting Carbonyl Chloride | Starting R'-YH compound |
|---|---|---|---|---|
| 5 MM058 | 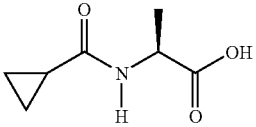 2-(Cyclopropanecarbonyl-amino)-propionic acid | 157.17 | P | Methyl ester alanine hydrochloride (Amino Acid) |
| 6 MM059 | 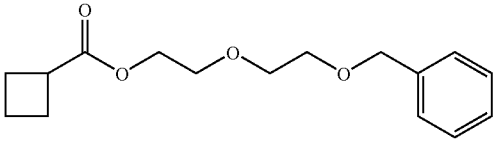 Cyclobutanecarboxylic acid 2-(2-benzyloxy-ethoxy)-ethyl ester | 278.34 | B | 2-(2-Benzyl-oxy-eth-oxy)-ethanol |
| 7 MM060 | 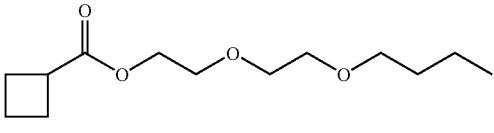 Cyclobutanecarboxylic acid, 2-(2-butoxy-ethoxy)-ethyl ester | 244.32 | B | 2-(2-Butoxy-eth-oxy)-ethanol |
| 8 MM061 | 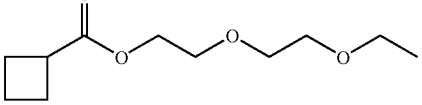 Cyclobutanecarboxylic acid, 2-(2-ethoxy-ethoxy)-ethyl ester | 216.27 | B | 2-(2-ethoxy-eth-oxy)-ethanol |
| 9 MM062 | 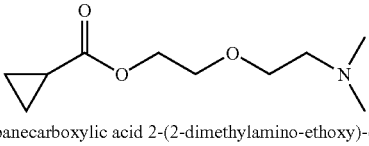 Cyclopropanecarboxylic acid 2-(2-dimethylamino-ethoxy)-ethyl ester | 201.26 | P | 2-(2-di-methylamino-eth-oxy)-ethanol |
| 10 MM063 | 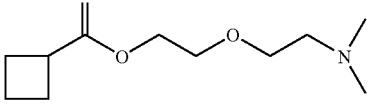 Cyclobutanecarboxylic acid 2-(2-dimethylamino-ethoxy)-ethyl ester | 215.29 | B | 2-(2-di-methylamino-eth-oxy)-ethanol |
| 11 MM064 | 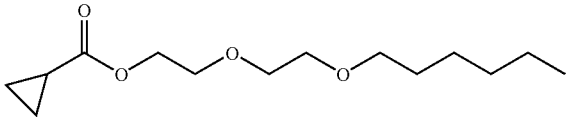 Cyclopropanecarboxylic acid 2-(2-hexyloxy-ethoxy)-ethyl ester | 258.35 | P | 2-(2-hexyl-oxy-eth-oxy)-ethanol |
| 12 MM065 | 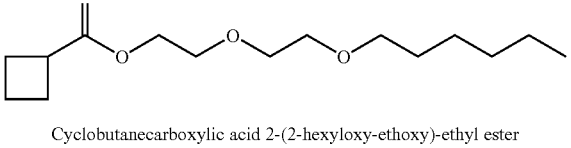 Cyclobutanecarboxylic acid 2-(2-hexyloxy-ethoxy)-ethyl ester | 272.39 | B | 2-(2-hexyl-oxy-eth-oxy)-ethanol |

TABLE 1-continued

| Example | Compound | Molecular Weight | Starting Carbonyl Chloride | Starting R'-YH compound |
|---|---|---|---|---|
| 13 MM066 | Cyclopropanecarboxylic acid 2-(2-methoxy-ethoxy)-ethyl ester | 188.23 | P | 2-(2-methoxy-ethoxy)-ethanol |
| 14 MM067 | Cyclobutanecarboxylic acid 2-(2-methoxy-ethoxy)-ethyl ester | 202.25 | B | 2-(2-methoxy-ethoxy)-ethanol |
| 15 MM068 | Cyclopropanecarboxylic acid 2-ethoxy-ethyl ester | 158.20 | P | 2-ethoxy-ethanol |
| 16 MM069 | Cyclobutanecarboxylic acid 2-ethoxy-ethyl ester | 172.23 | B | 2-ethoxy-ethanol |
| 17 MM070 | Cyclopropanecarboxylic acid 2-isopropoxy-ethyl ester | 172.23 | P | 2-Isopropoxy-ethanol |
| 18 MM071 | Cyclobutanecarboxylic acid 2-isopropoxy-ethyl ester | 186.25 | B | 2-Isopropoxy-ethanol |
| 19 MM072 | Cyclopropanecarboxylic acid, 2-(2-cyclopropanecarbonyloxy-ethoxy)-ethyl ester | 242.27 | P | 2-(2-Hydroxy-ethoxy)-ethanol |
| 20 MM073 | Cyclobutanecarboxylic acid, 2-(2-cyclobutanecarbonyloxy-ethoxy)-ethyl ester | 270.32 | B | 2-(2-Hydroxy-ethoxy)-ethanol |

TABLE 1-continued

| Example | Compound | Molecular Weight | Starting Carbonyl Chloride | Starting R'-YH compound |
|---|---|---|---|---|
| 21 MM074 | Cyclopropanecarboxylic acid, 2-[2-(2-cyclopropanecarbonyloxy-ethoxy)-ethoxy]ethyl ester | 286.32 | P | 2-[2-(2-Hydroxy-ethoxy)-ethoxy]-ethanol |
| 22 MM075 | Cyclobutanecarboxylic acid, 2-[2-(2-cyclobutanecarbonyloxy-ethoxy)-ethoxy}ethyl ester | 314.37 | B | 2-[2-(2-Hydroxy-ethoxy)-ethoxy]-ethanol |
| 23 MM076 | Cyclopropanecarboxylic acid 2-[{2-[bis(2-cyclopropanecarbonyloxy-ethyl)-amino]-ethyl}-(2-cyclopropanecarbonyloxy-ethyl)-amino]ethyl ester | 508.60 | P | N,N,N',N'-Tetrakis(2-hydroxyethyl)ethylenediamine |
| 24 MM077 | Cyclopropanecarboxylic acid(2-isopropoxy-ethyl)-amide | 171.24 | P | 2-Aminoethyl isopropyl ether |
| 25 MM078 | trans-2-Phenyl-cyclopropanecarboxylic acid 2-isopropoxy-ethyl ester | 248.32 | trans-2-phenyl-cyclopropanecarbonyl chloride | 2-Isopropoxy-ethanol |

TABLE 1-continued

| Example | Compound | Molecular Weight | Starting Carbonyl Chloride | Starting R'-YH compound |
|---|---|---|---|---|
| 26 MM079 | 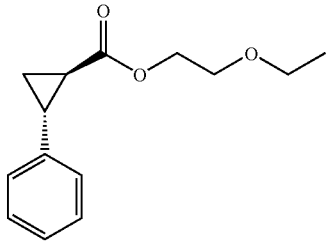 trans-2-Phenyl-cyclopropanecarboxylic acid 2-ethoxy-ethyl ester | 234.29 | trans-2-phenyl-cyclopropanecarbonyl chloride | 2-ethoxy-ethanol |
| 27 MM080 | 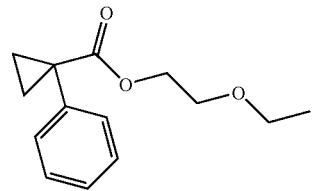 1-Phenyl-cyclopropanecarboxylic acid 2-ethoxy-ethyl ester | 234.29 | 1-phenyl-cyclopropanecarbonyl chloride | 2-ethoxy-ethanol | a. P* Cyclopropanecarbonyl chloride
b. B** Cyclobutanecarbonyl chloride

Example A

Glucose oxidation stimulation in untreated myocardium cells and myocardium cells treated with cyclopropanecarboxylic acid, 2-[2-(2-methoxy-ethoxy)-ethoxy]-ethyl ester. Rat hearts were cannulated for isolated working heart 60 min aerobic perfusions as described in *J Pharmacol Exp Ther.* 1993; 264:135–144, the entire disclosure of which is incorporated herein by reference.

Male Sprague-Dawley rats (0.3–0.35 kg) were anesthetized with pentobarbital sodium (60 mg/kg IP) and hearts were quickly excised, the aorta was cannulated and a retrograde perfusion at 37° C. was initiated at a hydrostatic pressure of 60 mm Hg. Hearts were trimmed of excess tissue, and the pulmonary artery and the opening to the left atrium were then cannulated. After 15 min of Langendorff perfusion; hearts were switched to the working mode by clamping the aortic inflow line from the Langendorff reservoir and opening the left atrial inflow line. The perfusate was delivered from an oxygenator into the left atrium at a constant preload pressure of 11 mm Hg. Perfusate was ejected from spontaneously beating hearts into a compliance chamber (containing 1 ml of air) and into the aortic outflow line. The afterload was set at a hydrostatic pressure of 80 mm Hg. All working hearts were perfused with Krebs'-Henseleit solution containing calcium 2.5 mmol/L, glucose 5.5 mmol/L, 3% bovine serum albumin (fatty acid free, initial fractionation by heat shock, Sigma), and with 1.2 mmol/L palmitate. Palmitate was bound to the albumin as described in *J Bio Chem.* 1992; 267:3825–3831, the entire disclosure of which is incorporated herein by reference.

The perfusate was recirculated, and pH was adjusted to 7.4 by bubbling with a mixture containing 95% $O_2$ and 5% $CO_2$.

Spontaneously beating hearts were used in all perfusions. Heart rate and aortic pressure were measured with a Biopac Systems Inc. blood pressure transducer connected to the aortic outflow line. Cardiac output and aortic flow were measured with Transonic T206 ultrasonic flow probes in the preload and afterload lines, respectively. Coronary flow was calculated as the difference between cardiac output and aortic flow. Cardiac work was calculated as the product of systolic pressure and cardiac output.

Measurement of Glucose Oxidation: Glucose oxidation was measured simultaneously by perfusing hearts with [U-$^{14}$C] glucose according to the procedures discussed in Saddik M, et al., *J Bio Chem.* 1992; 267:3825–3831. The entire disclosure of this reference is incorporated herein by reference. The total myocardial $^{14}CO_2$ production was determined at 10-min intervals from the 60-min aerobic period. Glucose oxidation rates were determined by quantitative measurement of $^{14}CO_2$ production as described in Barbour R L, et al., *Biochemistry.* 1984; 1923:6503–6062. The entire disclosure of this reference is incorporated herein by reference. $^{14}CO_2$ production for the control group were compared with the $^{14}CO_2$ production for the group treated with cyclopropanecarboxylic acid, 2-[2-(2-methoxy-ethoxy)-ethoxy]-ethyl ester. Results are shown on FIG. 1 and TABLE 2.

Example B (1) Glucose oxidation stimulation in myocardium cells treated with cyclobutanecarboxylic acid, 2-[2-(2-methoxy-ethoxy)-ethoxy]-ethyl ester.

Figure 2:
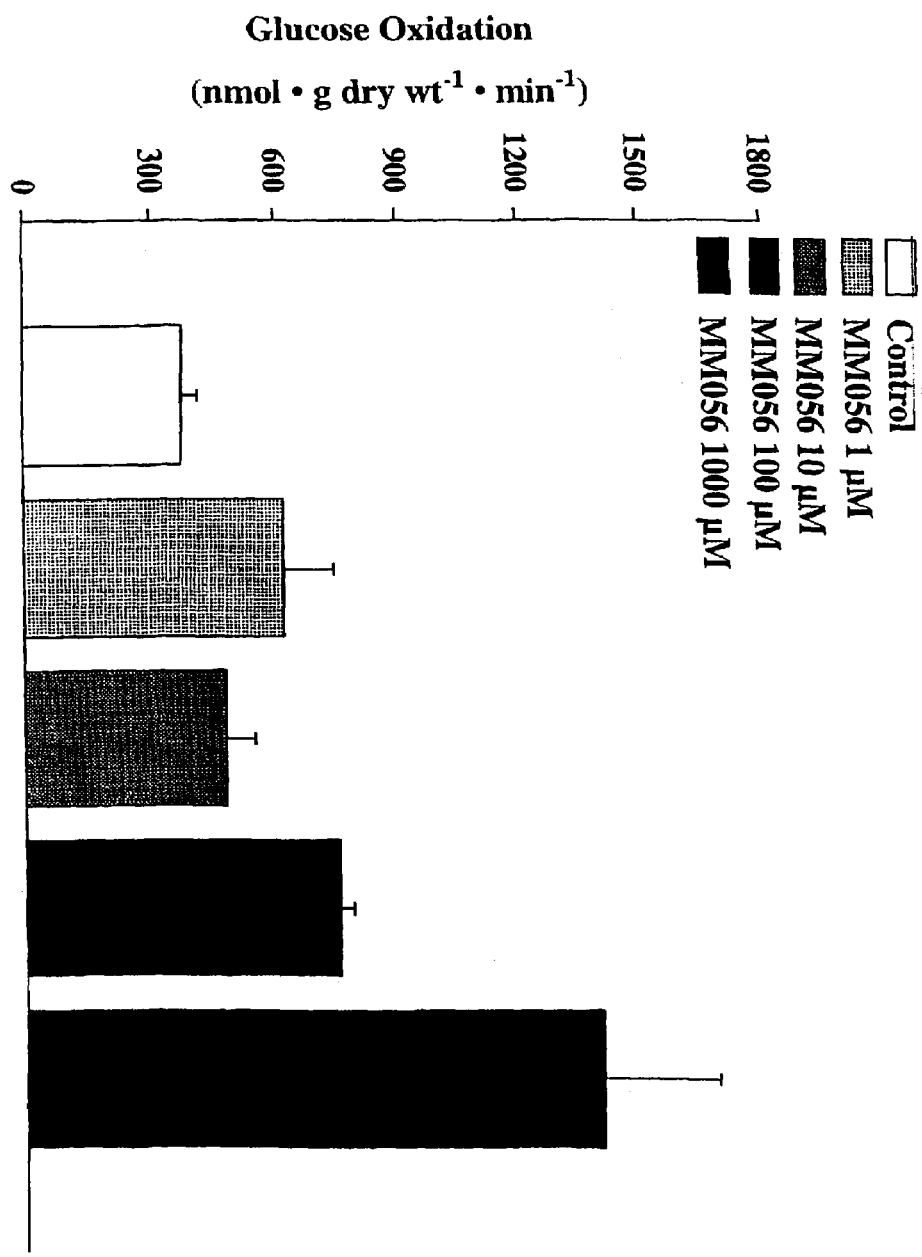
FIG. 2 is a graph which depicts glucose oxidation in an isolated perfused working rat heart model at the indicated concentrations of cyclobutanecarboxylic acid, 2-[2-(2-methoxy-ethoxy)-ethoxy]-ethyl ester (MM056) as compared to a control.

The procedure of Example A for was followed except that cyclobutanecarboxylic acid, 2-[2-(2-methoxy-ethoxy)-ethoxy]-ethyl ester in 1 µM, 10 µM, 100 µM and 1000 µM amounts was added to the buffer in place of the cyclopropanecarboxylic acid, 2-[2-(2-methoxy-ethoxy)-ethoxy]-ethyl ester. The results are illustrated in FIG. 2 and TABLE 2.

(2) Glucose oxidation stimulation in myocardium cells treated with cyclopropanecarboxylic acid, 2-isopropoxy ethyl ester.

Figure 3:
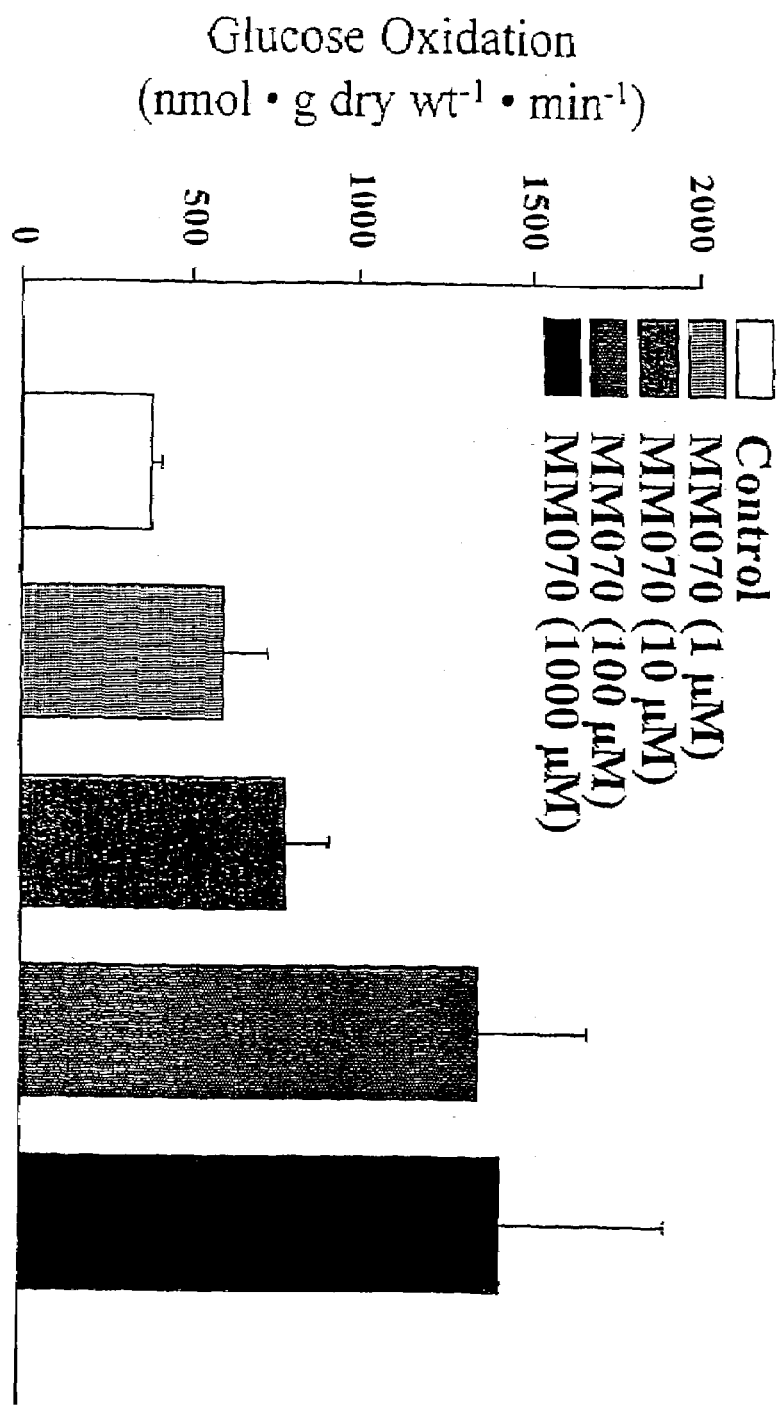
FIG. 3 is a graph which depicts glucose oxidation in an isolated perfused working rat heart model at increasing concentrations of cyclopropanecarboxylic acid, 2-isopropoxy-ethyl ester (MM070) as compared to a control.

The procedure of Example A was followed except that cyclopropanecarboxylic acid, 2-isopropoxy-ethyl ester in 1 µM, 10 µM, 100 µM and 1000 µM amounts was added to the buffer in place of the cyclopropanecarboxylic acid, 2-[2-(2-methoxy-ethoxy)-ethoxy]-ethyl ester. The results are illustrated in FIG. 3 and TABLE 2.

(3) Glucose oxidation stimulation in myocardium cells treated with various cyclopropanecarboxylic acid and cyclobutanecarboxylic acid derivatives.

The procedure of Example A was followed except that various cyclobutanecarboxylic acid derivatives, cyclopropanecarboxylic acid derivatives and cyclobutanecarboxylic acid in the amounts of 100 µM or 1000 µM was added to the buffer in place of the cyclopropanecarboxylic acid, 2-[2-(2-methoxy-ethoxy)-ethoxy]-ethyl ester. The results are illustrated in TABLE 2.

(4) Glucose oxidation stimulation in myocardium cells treated with cyclopropanecarboxylic acid.

Figure 4:
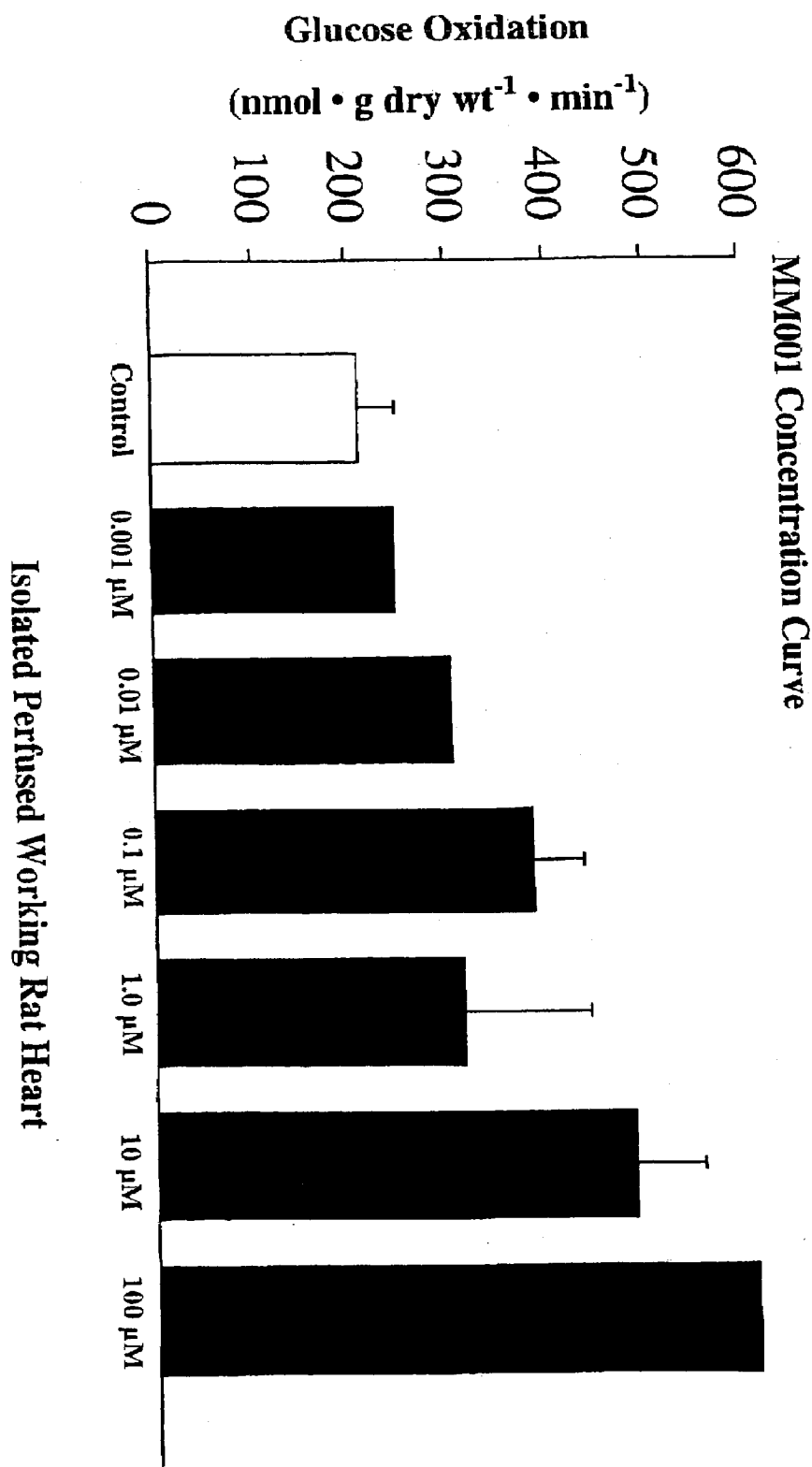
FIG. 4 is a graph which depicts glucose oxidation in an isolated perfused working rat heart model at increasing concentrations of cyclopropanecarboxylic acid (MM001) as compared to a control.

The procedure of Example A was followed except that cyclobutanecarboxylic acid the amounts of 0.001 µM, 0.01 µM, 01 µM, 1 µM, 10 µM, and 100 µM was added to the buffer in place of the cyclopropanecarboxylic acid, 2-[2-(2-methoxy-ethoxy)-ethoxy]-ethyl ester. The results are illustrated in FIG. 4 and TABLE 2.

TABLE 2

| Compound of Example No. | Compound | | Screening Concentration (µM) | Glucose Oxidation (% above control) |
|---|---|---|---|---|
| 1 MM054 | 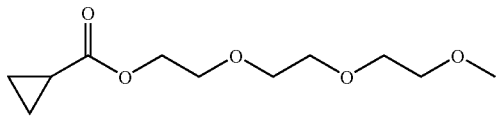 Cyclopropanecarboxylic acid 2-[2-(2-methoxy-ethoxy)-ethoxy]-ethyl ester | | 100 | 102% |
| 2 MM055 | 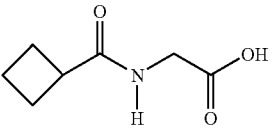 (Cyclobutanecarbonyl-amino)-acetic acid | | 1000 µM | 58% |
| 3 MM056 | 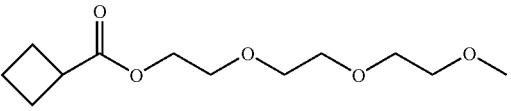 Cyclobutanecarboxylic acid 2-[2-(2-methoxy-ethoxy)-ethoxy]-ethyl ester | | 100 µM | 54% |
| 4 MM057 | 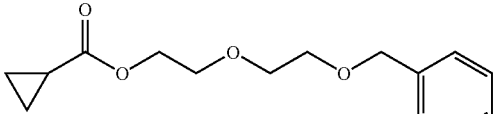 Cyclopropanecarboxylic acid 2-(2-benzyloxy-ethoxy)-ethyl ester | | 100 µM | 104% |
| 5 MM058 | 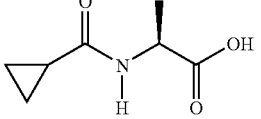 2-(Cyclopropanecarbonyl-amino)-propionic acid | | 1000 µM | 40% |
| 6 MM059 | 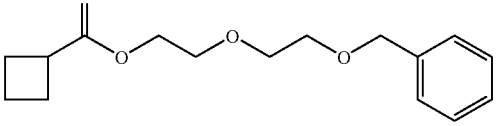 Cyclobutanecarboxylic acid 2-(2-benzyloxy-ethoxy)-ethyl ester | | 100 µM | 68% |

TABLE 2-continued

| Compound of Example No. | Compound | Screening Concentration (μM) | Glucose Oxidation (% above control) |
|---|---|---|---|
| 7 MM060 | 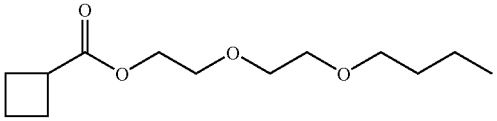 Cyclobutanecarboxylic acid, 2-(2-butoxy-ethoxy)-ethyl ester | 100 μM | 65% |
| 8 MM061 | 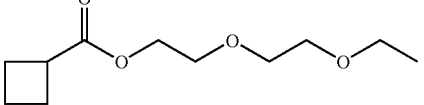 Cyclobutanecarboxylic acid, 2-(2-ethoxy-ethoxy)-ethyl ester | Not screened | |
| 9 MM062 | 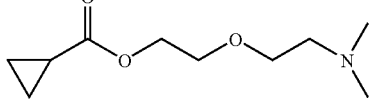 Cyclopropanecarboxylic acid 2-(2-dimethylamino-ethoxy)-ethyl ester | 100 μM | 77% |
| 10 MM063 | 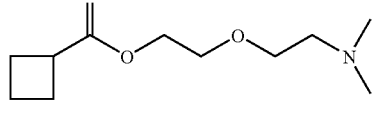 Cyclobutanecarboxylic acid 2-(2-dimethylamino-ethoxy)-ethyl ester | 100 μM | 41% |
| 11 MM064 | 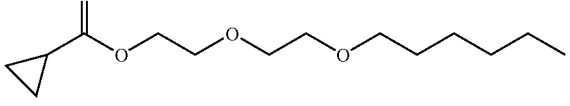 Cyclopropanecarboxylic acid 2-(2-hexyloxy-ethoxy)-ethyl ester | 100 μM | 83% |
| 12 MM065 | 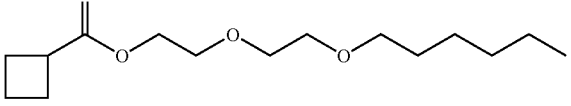 Cyclobutanecarboxylic acid 2-(2-hexyloxy-ethoxy)-ethyl ester | 100 μM | 0% |
| 13 MM066 | 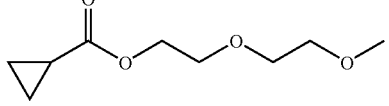 Cyclopropanecarboxylic acid 2-(2-methoxy-ethoxy)-ethyl ester | 100 μM | 20% |
| 14 MM067 | 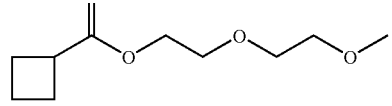 Cyclobutanecarboxylic acid 2-(2-methoxy-ethoxy)-ethyl ester | 100 μM | 50% |

TABLE 2-continued

| Compound of Example No. | Compound | Screening Concentration (µM) | Glucose Oxidation (% above control) |
|---|---|---|---|
| 15 MM068 | 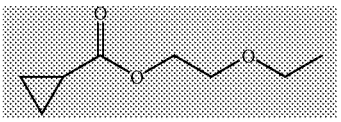<br>Cyclopropanecarboxylic acid 2-ethoxy-ethyl ester | 100 µM | 416% |
| 16 MM069 | 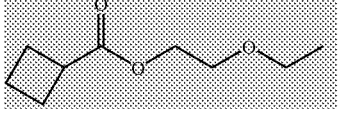<br>Cyclobutanecarboxylic acid 2-ethoxy-ethyl ester | 100 µM | 162% |
| 17 MM070 | 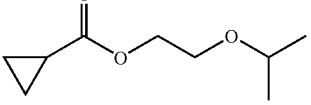<br>Cyclopropanecarboxylic acid 2-isopropoxy-ethyl ester | 100 µM | 208% |
| 18 MM071 | 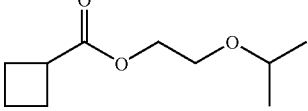<br>Cyclobutanecarboxylic acid 2-isopropoxy-ethyl ester | 100 µM | 97% |
| 19 MM072 | 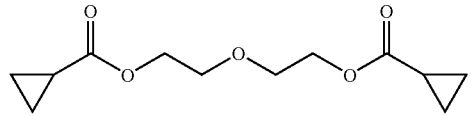<br>Cyclopropanecarboxylic acid, 2-(2-cyclopropanecarbonyloxy-ethoxy)-ethyl ester | 100 µM | 97% |
| 20 MM073 | 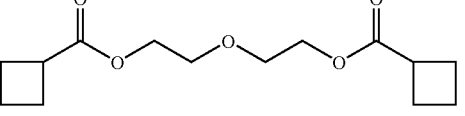<br>Cyclobutanecarboxylic acid, 2-(2-cyclobutanecarbonyloxy-ethoxy)-ethyl ester | 100 µM | 243% |
| 21 MM074 | 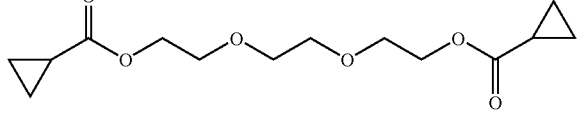<br>Cyclopropanecarboxylic acid, 2-[2-(2-cyclopropanecarbonyloxy-ethoxy)-ethoxy]ethyl ester | 100 µM | 228% |
| 22 MM075 | 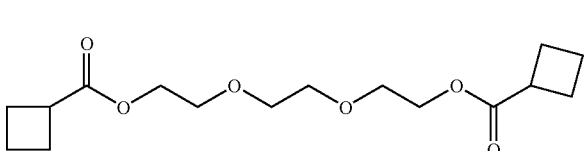<br>Cyclobutanecarboxylic acid, 2-[2-(2-cyclobutanecarbonyloxy-ethoxy)-ethoxy]-ethyl ester | 100 µM | 184% |

TABLE 2-continued

| Compound of Example No. | Compound | Screening Concentration (μM) | Glucose Oxidation (% above control) |
|---|---|---|---|
| 23 MM076 | Cyclopropanecarboxylic acid 2-[{2-[bis(2-cyclopropanecarbonyloxy-ethyl)-amino]-ethyl}-(2-cyclopropanecarbonyloxy-ethyl)-amino]ethyl ester | 100 μM | 274% |
| 24 MM077 | Cyclopropanecarboxylic acid(2-isopropoxy-ethyl)-amide | 100 μM | 217% |
| 25 MM078 | trans-2-Phenyl-cyclopropanecarboxylic acid 2-isopropoxy-ethyl ester | 100 μM | 200% |
| 26 MM079 | trans-2-Phenyl-cyclopropanecarboxylic acid 2-ethoxy-ethyl ester | not screened | |

TABLE 2-continued

| Compound of Example No. | Compound | Screening Concentration (μM) | Glucose Oxidation (% above control) |
|---|---|---|---|
| 27 MM080 | 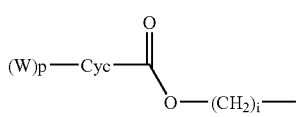<br>1-Phenyl-cyclopropanecarboxylic acid 2-ethoxy-ethyl ester | | not screened |

A number of embodiments of the invention have been described. Nevertheless, it will be understood that various modifications may be made without departing from the spirit and scope of the invention.

What is claimed is:

1. A sterile injectable pharmaceutical composition comprising a physiologically acceptable carrier and a glucose utilization increasing amount of at least one compound represented by Formula (I):

Formula (I)

wherein

W is $C_1$–$C_6$ alkyl, halogen, or aryl;

Cyc is $C_3$ or $C_4$ cycloalkyl;

p is an integer from 0 to 3 when Cyc is $C_4$ cycloalkyl, or p is 0 to 2 when Cyc is $C_3$ cycloalkyl;

Y is O, S, or NR;

X is O, S, NR, or $CR^3R^4$;

Z is if X is NR and R is

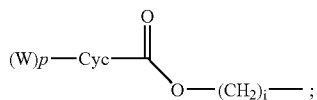

R is H, alkyl, aryl, or

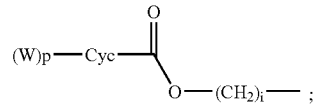

where i is an integer from 2 to 4;

$R^1$ is H, alkyl or aryl;

$R^2$ is H, alkyl, aryl or O;

$R^3$ and $R^4$ are, independently, H, alkyl or aryl; and n is an integer from 1 to 10; or a pharmaceutically acceptable salt, ester or prodrug thereof; and a pharmaceutically acceptable carrier, diluent, excipient or mixtures thereof.

2. A pharmaceutical composition according to claim 1, wherein said composition is in the form of sterile suspensions or solutions.

3. A pharmaceutical composition according to claim 1, wherein said at least one compound is selected from the group consisting of cyclopropanecarboxylic acid, 2-(2-cyclopropanecarbonyloxy-ethoxy)-ethyl ester;

cyclopropanecarboxylic acid, 2-[2-(2-cyclopropanecarbonyloxy-ethoxy)-ethoxy]-ethyl ester;

cyclobutanecarboxylic acid, 2-[2-(2-cyclobutanecarbonyloxy-ethoxy)-ethoxy]-ethyl ester;

cyclobutanecarboxylic acid 2,(2-cyclobutanecarbonyloxy-ethoxy)-ethyl ester; and cyclopropanecarboxylic acid 2-[{2-(bis(2-cyclopropanecarbonyloxy-ethyl)-amino]-ethyl}-(2-cyclopropanecarbonuloxy-ethyl)-amino)]ethyl ester.

4. A method for increasing glucose utilization in a cell, tissue or organ of a warm blooded animal comprising treating said cell, tissue or organ with glucose utilization effective amount of at least one compound represented by Formula (I)

Formula (Ia)

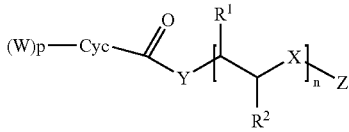

wherein
W is $C_1$–$C_6$ alkyl, halogen, or aryl;
Cyc is $C_3$ or $C_4$ cycloalkyl;
p is an integer from 0 to 3 when Cyc is $C_4$ cycloalkyl, or
  p is an integer from 0 to 2 when Cyc is $C_3$ cycloalkyl;
Y is O, S, or NR;
X is O, S, NR, or $CR^3R^4$;
Z is

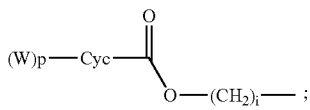

if X is NR and R is

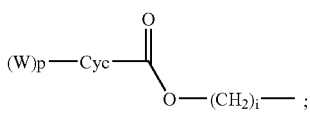

R is H, alkyl, aryl or

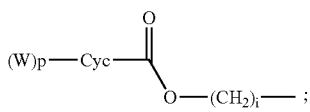

where i is an integer from 2 to 4;
$R^1$ is H, alkyl or aryl;
$R^2$ is H, alkyl, aryl or O;
$R^3$ and $R^4$ are, independently, H, alkyl or aryl; and
n is an integer from 1 to 10; or a pharmaceutically acceptable salt, ester or prodrug thereof.

5. A method according to claim 4, wherein said compound is represented by Formula (II), wherein p is 0.

6. A method according to claim 4, wherein said organ is heart.

7. A method according to claim 4, wherein said cell is a myocardial cell.

8. The method according to claim 4, wherein said at least one compound is selected from the group consisting of
cyclopropanecarboxylic acid, 2-(2-cyclopropanecarbonyloxy-ethoxy)-ethyl ester;
cyclopropanecarboxylic acid, 2-[2-(2-cyclopropanecarbonyloxy-ethoxy)-ethoxy]-ethyl ester;
cyclobutanecarboxylic acid, 2-[2-(2-cyclobutanecarbonyloxy-ethoxy)-ethoxy]-ethyl ester;
cyclobutanecarboxylic acid 2,(2-cyclobutanecarbonyloxy-ethoxy)-ethyl ester; and
cyclopropanecarboxylic acid 2-[{2-(bis(2-cyclopropanecarbonyloxy-ethyl)-amino]ethyl}-(2-cyclopropanecarbonyloxy-ethyl)-amino)]ethyl ester.

9. A method for treatment of physiological conditions or disorders treatable by increasing glucose utilization comprising:
administering to a patient in need of such treatment, effective amount to increase glucose utilization of a pharmaceutical composition comprising at least one compound represented by Formula (I)

Formula (I)

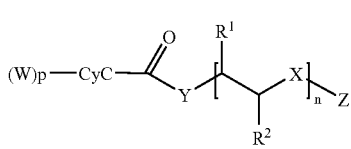

wherein
W is $C_1$–$C_6$ alkyl, halogen, or aryl;
Cyc is $C_3$ or $C_4$ cycloalkyl;
p is an integer from 0 to 3 when Cyc is $C_4$ cycloalkyl, or
  p is an integer from 0 to 2 when Cyc is $C_3$ cycloalkyl;
Y is O, S, or NR;
X is O, S, NR, or $CR^3R^4$;
Z is

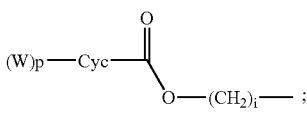

if X is NR and R is

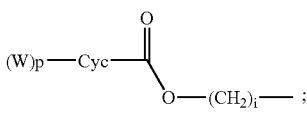

R is H, alkyl, aryl or

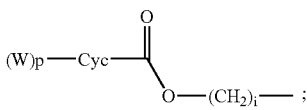

where i is an integer from 2 to 4;
$R^1$ is H, alkyl or aryl;
$R^2$ is H, alkyl, aryl or O;
$R^3$ and $R^4$ are, independently, H, alkyl or aryl; and
n is an integer from 1 to 10; or a pharmaceutically acceptable salt, ester or prodrug thereof.

10. A method according to claim 9, wherein said disorder or condition is ischemic/reperfusion injury, post myocardial infarction, angina, heart failure, a cardiomyopathy, peripheral vascular disease, diabetes, and lactic acidosis, or symptoms or side effects associated with open heart surgery, bypass surgery, or heart transplant.

11. A method according to claim 10, wherein said disorder or condition is ischemic/reperfusion injury.

12. The method according to claim 9, wherein said at least one compound is selected from the group consisting of
cyclopropanecarboxylic acid, 2-(2-cyclopropanecarbonyloxy-ethoxy)-ethyl ester;

cyclopropanecarboxylic acid, 2-[2-(2-cyclopropanecarbonyloxy-ethoxy)-ethoxy]-ethyl ester;

cyclobutanecarboxylic acid, 2-[2-(2-cyclobutanecarbonyloxy-ethoxy)-ethoxy]-ethyl ester;

cyclobutanecarboxylic acid 2,(2-cyclobutanecarbonyloxy-ethoxy)-ethyl ester; and cyclopropanecarboxylic acid 2-[{2-(bis(2-cyclopropanecarbonyloxy-ethyl)-amino]-ethyl}-(2-cyclopropanecarbonuloxy-ethyl)-amino)]ethyl ester.

13. A kit containing a pharmaceutical composition according to claim 1.

14. A kit according to claim 13, wherein said kit comprises a label or packaging insert containing instructions for use, in vitro, in vivo, or ex vivo, of components of said kit.

15. A composition according to claim 1 wherein Y is O, X is NR or O, n is 1 to 4, p is O; $R^1$, $R^2$, $R^3$ and $R^4$ are hydrogen; and Z is

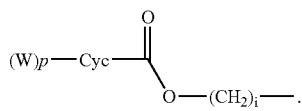

16. A composition according to claim 1 wherein Y is O, X is NR, n is 1 to 4, p is O; $R^1$, $R^2$, $R^3$ and $R^4$ are hydrogen; and Z is

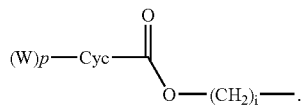

17. A composition according to claim 16 wherein i is 2.

18. A composition according to claim 17 wherein n is 2.

19. A composition according to claim 18 wherein R is

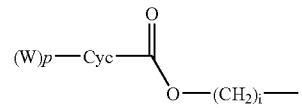

and Z is

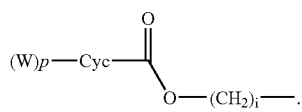

20. A composition according to claim 19 wherein Cyc is $C_3$ cycloalkyl.

21. An oral pharmaceutical composition in unit dosage form comprising a glucose utilization increasing amount of at least one compound represented by Formula (I):

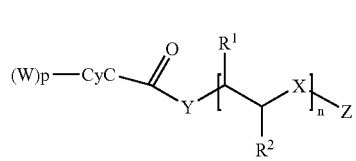

Formula (I)

wherein

W is $C_1$–$C_6$ alkyl, halogen, or aryl;

Cyc is $C_3$ or $C_4$ cycloalkyl;

p is an integer from 0 to 3 when Cyc is $C_4$ cycloalkyl, or p is 0 to 2 when Cyc is $C_3$ cycloalkyl;

Y is O, S, or NR;

X is O, S, NR, or $CR^3R^4$;

Z is

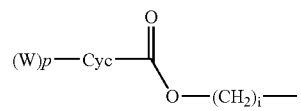

if X is NR and R is

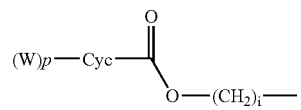

R is H, alkyl, aryl, or

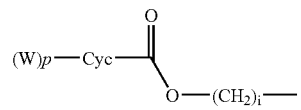

where i is an integer from 2 to 4;

$R^1$ is H, alkyl or aryl;

$R^2$ is H, alkyl, aryl or O;

$R^3$ and $R^4$ are, independently, H, alkyl or aryl; and n is an integer from 1 to 10; or a pharmaceutically acceptable salt, ester or prodrug thereof; and a pharmaceutically acceptable carrier, diluent, excipient or mixtures thereof.

22. An oral pharmaceutical composition according to claim 21, wherein said composition is in the form of tablets, pills, or capsules.

23. An oral pharmaceutical composition according to claim 21, wherein said at least one compound is selected from the group consisting of cyclopropanecarboxylic acid, 2-(2-cyclopropanecarbonyloxy-ethoxy)-ethyl ester;

cyclopropanecarboxylic acid, 2-[2-(2-cyclopropanecarbonyloxy-ethoxy)-ethoxy]-ethyl ester;

cyclobutanecarboxylic acid, 2-[2-(2-cyclobutanecarbonyloxy-ethoxy)-ethoxy]-ethyl ester;

cyclobutanecarboxylic acid 2,(2-cyclobutanecarbonyloxy-ethoxy)-ethyl ester; and cyclopropanecarboxylic acid 2-[{2-(bis(2-cyclopropanecarbonyloxy-ethyl)-amino]-ethyl}-(2-cyclopropanecarbonyloxy-ethyl)-amino)]ethyl ester.

24. A kit containing an oral pharmaceutical composition according to claim 21.

25. A kit according to claim 24, wherein said kit comprises a label or packaging insert containing instructions for use, in vitro, in vivo, or ex vivo, of components of said kit.

26. A composition according to claim 21 wherein Y is O, X is NR or O, n is 1 to 4, p is O; $R^1$, $R^2$, $R^3$ and $R^4$ are hydrogen; and Z is

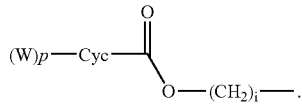

27. A composition according to claim 21 wherein Y is O, X is NR, n is 1 to 4, p is O; $R^1$, $R^2$, $R^3$ and $R^4$ are hydrogen; and Z is

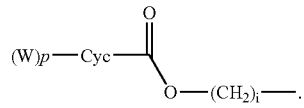

28. A composition according to claim 26 wherein i is 2.

29. A composition according to claim 27 wherein n is 2.

30. A composition according to claim 28 wherein R is

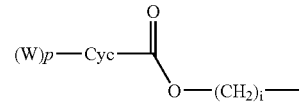

and Z is

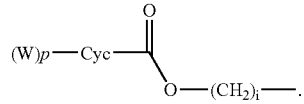

31. A composition according to claim 29 wherein Cyc is $C_3$ cycloalkyl.

* * * * *